US011628033B2

(12) United States Patent
Steiner

(10) Patent No.: US 11,628,033 B2
(45) Date of Patent: Apr. 18, 2023

(54) OPERATING TABLE BARRIERS AND METHODS OF USE THEREOF

(71) Applicant: LTZ Industries LLC, Brooklyn, NY (US)

(72) Inventor: Max Steiner, Brooklyn, NY (US)

(73) Assignee: LTZ Industries LLC, Brooklyn, NY (US)

( * ) Notice: Subject to any disclaimer, the term of this patent is extended or adjusted under 35 U.S.C. 154(b) by 202 days.

(21) Appl. No.: 16/983,725

(22) Filed: Aug. 3, 2020

(65) Prior Publication Data

US 2022/0031419 A1 Feb. 3, 2022

(51) Int. Cl.

| | |
|---|---|
| ***A61B 90/00*** | (2016.01) |
| ***A61G 13/10*** | (2006.01) |
| *A61M 25/02* | (2006.01) |
| *A61M 16/08* | (2006.01) |

(52) U.S. Cl.

CPC ............ *A61B 90/05* (2016.02); *A61G 13/101* (2013.01); *A61M 16/08* (2013.01); *A61M 2025/028* (2013.01)

(58) Field of Classification Search

CPC ..... A61B 90/00; A61B 90/04; A61B 90/0427; A61B 90/0436; A61B 90/05; A61G 10/00; A61G 15/00; A61G 15/10; A61G 13/101; A61G 10/005; A61M 16/08; A61M 2025/028

See application file for complete search history.

(56) References Cited

U.S. PATENT DOCUMENTS

| | | | | |
|---|---|---|---|---|
| 3,813,092 A * | 5/1974 | Foster | A61M 16/009 | 128/200.24 |
| 5,018,534 A * | 5/1991 | Grant | A61M 25/02 | 128/877 |
| 2002/0108614 A1* | 8/2002 | Schultz | A61M 16/0486 | 128/207.14 |
| 2017/0145711 A1* | 5/2017 | Esses | E04H 15/008 | |

* cited by examiner

*Primary Examiner* — Fredrick C Conley

(74) *Attorney, Agent, or Firm* — Lerner David LLP

(57) ABSTRACT

In one embodiment, a barrier includes two side panels extending on parallel planes and spaced laterally apart. Each side panel including a back end, a front edge opposed to the back end, a bottom edge, and an engagement feature on the bottom edge of each side panel. A back panel connects the side panels at the back ends, and a shield extends from an upper end of the back panel at an oblique angle in an upward and forward direction.

22 Claims, 22 Drawing Sheets

42 14 10 46 18 38 34 58 30 54 26 50 48

710 714 718 738 738 734 731 737 732 734 726 736 737 730 730 731 736 726 731

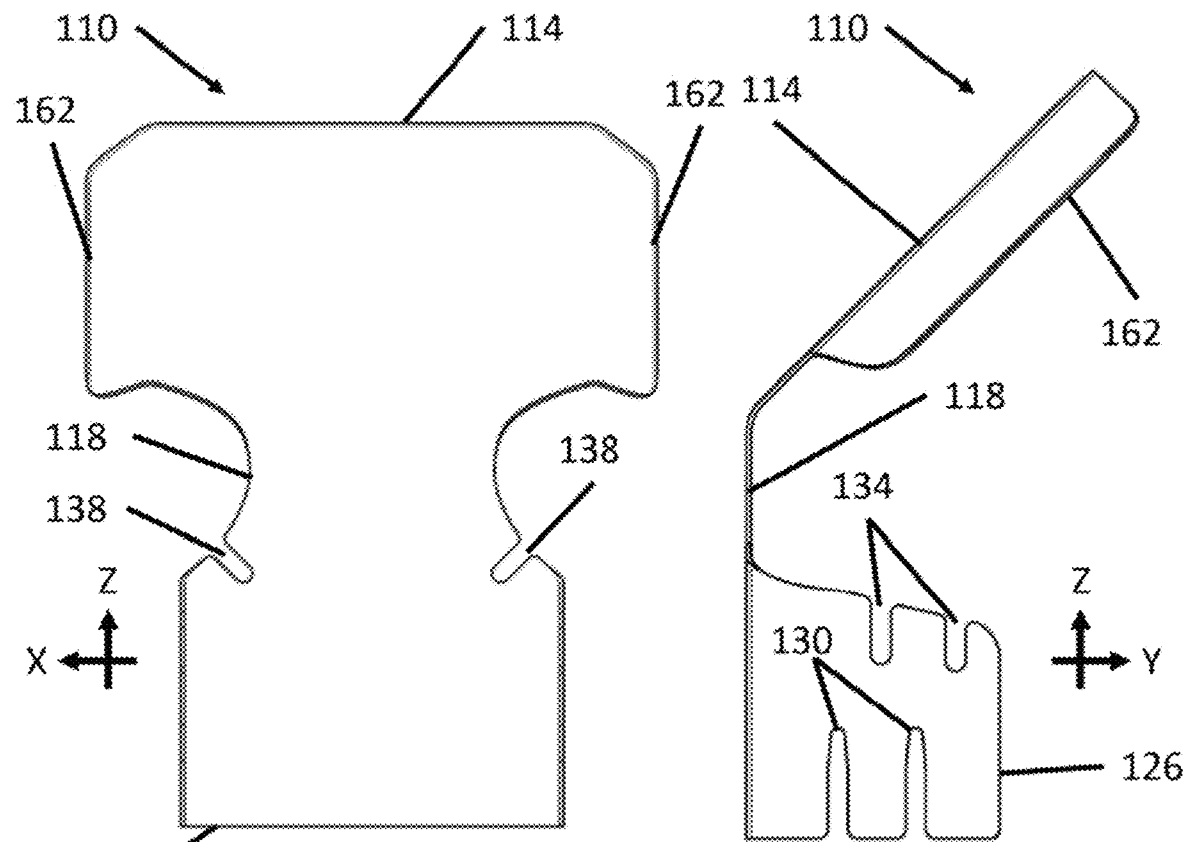
110
114
162
162
118
138
138
Z
X
122
FIG. 2B
110
162 114
162
118
134
130
Z
Y
126
FIG. 2C
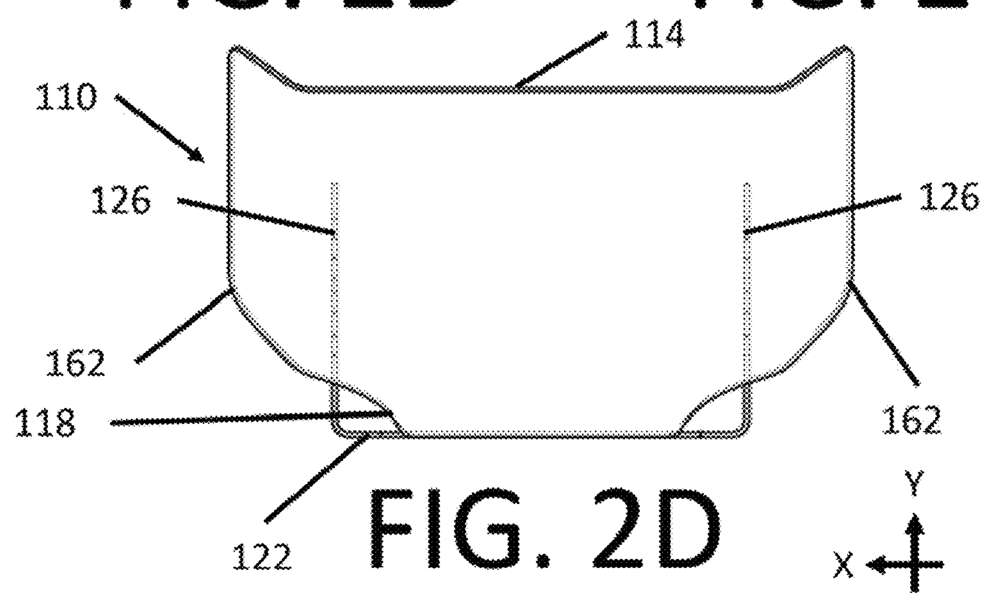
114
110
126
126
162
118
162
122
FIG. 2D
Y
X

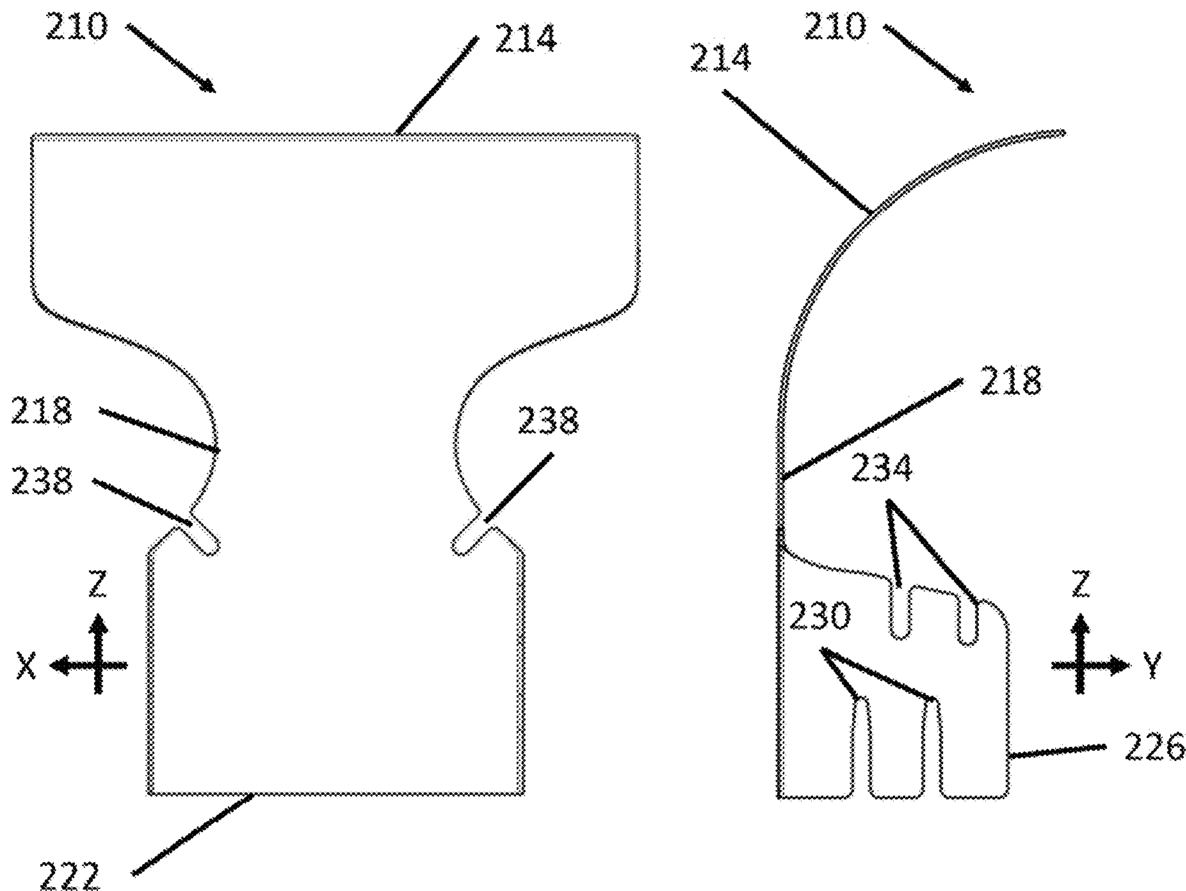
FIG. 3B
FIG. 3C
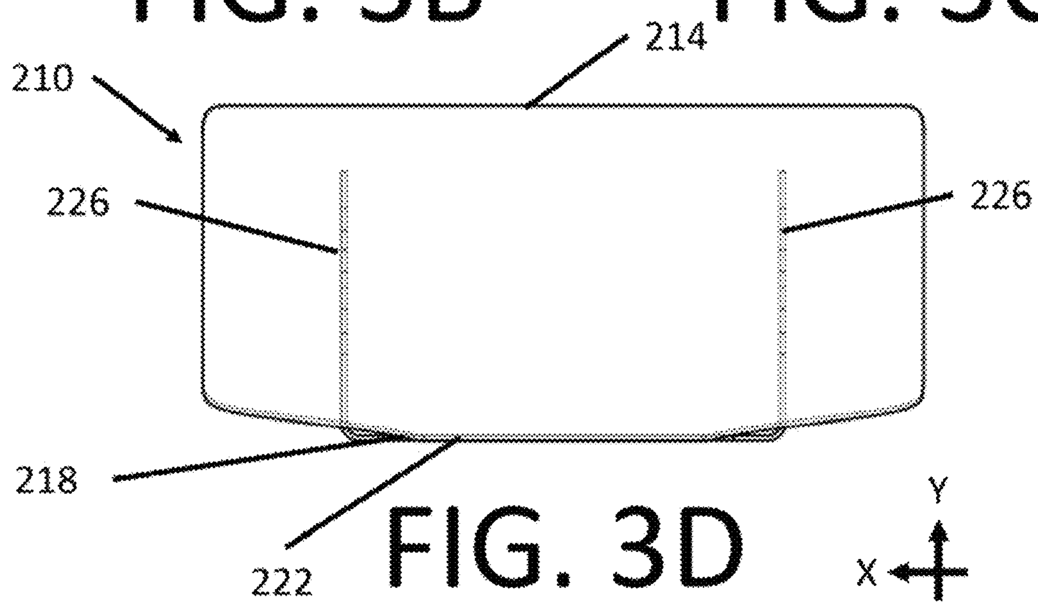
FIG. 3D

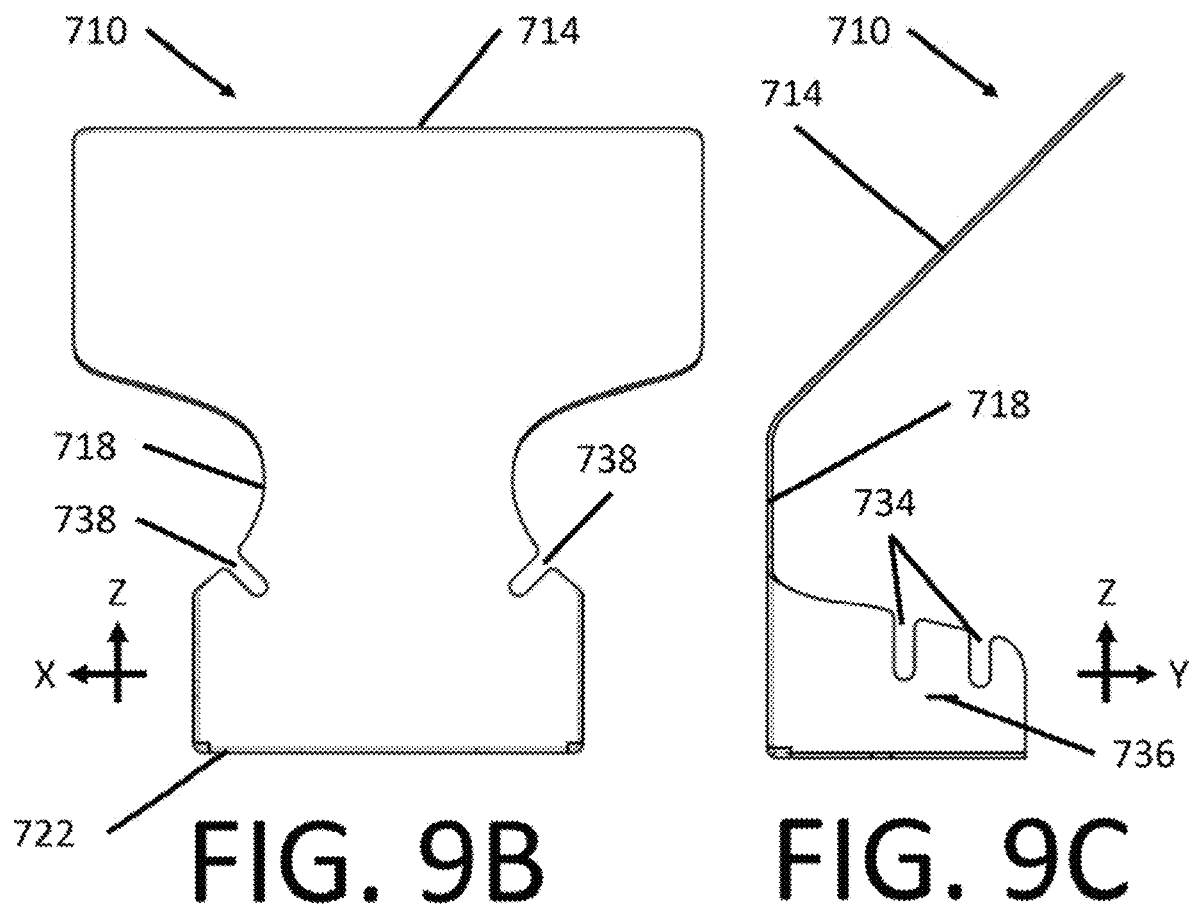
FIG. 9B
FIG. 9C
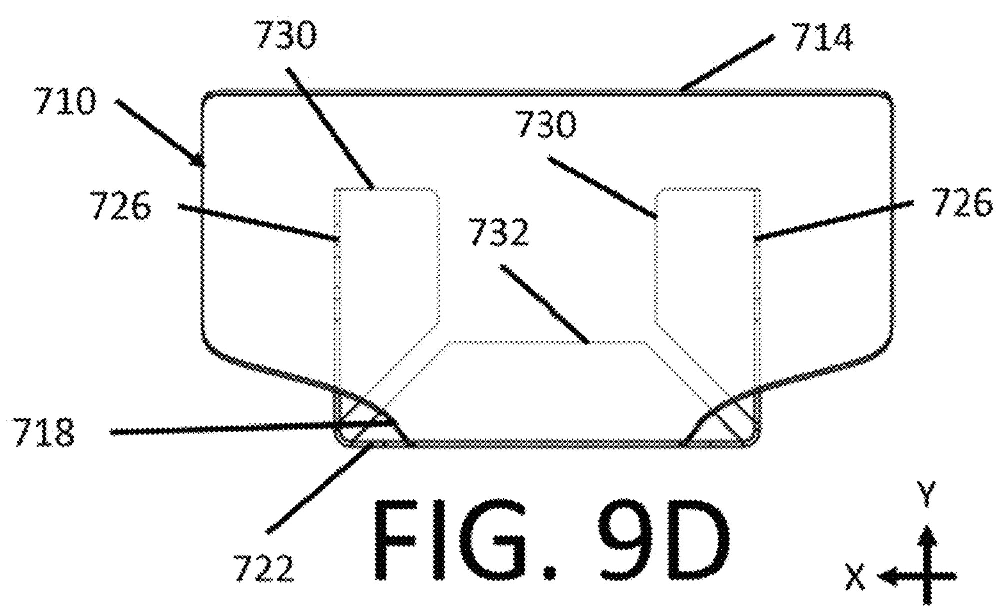
FIG. 9D

OPERATING TABLE BARRIERS AND METHODS OF USE THEREOF

BACKGROUND

Interaction between a healthcare worker and a patient can facilitate transmission of infectious disease, either from patient to healthcare worker or conversely from healthcare worker to patient. This is of particular importance in the operating room, where healthcare workers come into close proximity to the patient's airway, which is often the source of infectious respiratory diseases. The induction of anesthesia, administration of oxygen, positive pressure mask ventilation, placement of an advanced oropharyngeal airway, and endotracheal intubation are common potentially aerosolizing procedures that take place everyday in the operating room. Routine events such as bucking, coughing, oropharyngeal suction, endotracheal tube cuff leaks, can emit high viral loads in close proximity to the healthcare worker. During potential outbreaks of airborne respiratory diseases, such as COVID-19, enhancing the safety and minimizing the exposure of healthcare workers to potentially deadly pathogens during these common procedures is of paramount importance.

While protection of the healthcare worker during such procedures is important, also important is the ability of the healthcare worker to maintain rapid and bimanual free access to the patient. Currently used barriers for such procedures, such as intubation boxes, are cumbersome, time consuming to access, and greatly limit the range of motion for the healthcare worker during airway management. Typically, the healthcare worker must access the patient via arm holes, which provide only a single access point into the intubation box and to the patient. This can be very constricting for the healthcare worker, and can potentially restrict the speed of the procedure or limit its success rate during critical perioperative procedures.

Another disadvantage of such currently used devices is that the barrier is a confined space and could result in retention of carbon dioxide in a spontaneously breathing patient. If open source oxygen was being administered, the box could entrain oxygen and become a fire hazard. Lastly, water vapor or secretions could obscure the interior of the box and make visualization of the patient a challenge.

It would therefore be beneficial for a healthcare worker to be able to access the airway of a patient in a rapid manner that allows freedom of movement by the worker relative to the patient, while also maintaining a barrier between the worker's face and droplets and/or aerosols emitted from the patient's airway or from associated medical equipment.

BRIEF SUMMARY

According to an aspect of the disclosure, a barrier includes an attachment portion for engagement with an existing hospital bed, and a panel extending from the attachment point, where the panel is positioned between the patient and the healthcare worker. The attachment portion may have a structure capable of engagement with existing structures on the bed, such as for example a bed frame typically found around the perimeter of the bed. The barrier may be used to prevent direct transmission of aerosols from the patient and/or medical equipment to the healthcare worker, while also allowing for access to the patient by the healthcare worker.

In one embodiment, the barrier includes a pair of side panels spaced laterally apart by a distance corresponding to a width of a hospital bed. At least one slot may extend upward from lower edges of the side panels which correspond with post structures of a frame of the bed. The barrier may therefore be easily and removably engaged to the bed without modification to the bed itself.

Continuing with this embodiment, the barrier further includes a back panel, joining the two side panels at a location suitable for extending across an end of the bed when the slot(s) are placed over the posts, and a shield panel extending beyond the back panel. The shield may extend upward from the back panel, and may extend at an oblique angle away from the back panel and over the mattress and patient. The shield may be transparent. Further, the barrier may also include a relatively narrow neck portion between the back panel and the shield allowing a worker to reach around the barrier and access a patient while still remaining otherwise separated from the patient by the barrier. The barrier may include one or more additional slots extending into the neck or downward from upper edges of the side panels to hold tools or tubes used in treatment of the patient.

In another embodiment, a barrier includes two side panels extending on parallel planes and spaced laterally apart, each side panel including a back end, a front edge opposed to the back end, a bottom edge, and an engagement feature on the bottom edge of one or both side panels, a back panel connecting the side panels at the back ends, and a shield extending from an upper end of the back panel at an oblique angle in an upward and forward direction.

In some arrangements, the shield may include a neck that is laterally narrower than a distance between the two side panels.

In some arrangements, the neck may include two opposed lateral sides and at least one slot extending into the neck from at least one of the two lateral sides.

In some arrangements, the neck may be contiguous with the upper end of the back panel. Further, each of the panels, shield and the like may be monolithic or alternatively, one or more portions may be modular and capable of being connected together to form the barrier.

In some arrangements, the back panel may be planar and the lateral sides of the neck are concave.

In some arrangements, the shield may include a shield panel that extends upwards from the neck and includes a lateral distance equal to or beyond a lateral distance of the side panels.

In some arrangements, a first wing and a second wing may extend forward from each of two opposed lateral ends of the shield panel.

In some arrangements, the wings may extend laterally outward and forward on oblique planes.

In some arrangements, the shield may include a curve such that the shield panel curves in the forward and upward direction with increasing distance from the back panel.

In some arrangements, each side panel may include an upper edge opposed to the bottom edge and at least one slot extending downward from at least one of the upper edges.

In another embodiment, a method of manufacturing a barrier may comprise obtaining a planar sheet of transparent material, and preparing a shape from the sheet. The shape may include a lower base portion extending between two lower lateral edges, and a first tab and a second tab extending laterally from the two lower lateral edges of the lower base portion, each tab including a lower bottom edge including an engagement feature, an upper portion extending between two upper lateral edges, and a neck joining the lower portion and the upper portion, the neck extending between two middle lateral edges, a distance between the middle lateral edges being less than a distance between the two lower lateral edges and a distance between the two upper lateral edges. The method may further include bending the tabs in a forward direction relative to a remainder of the lower portion, and bending at least one of at least a portion of the upper portion and at least a portion of the neck forward relative to the lower base portion.

In some arrangements, the upper portion may include lateral wing portions extending from each upper lateral edge inwardly towards a middle area of the upper portion, the method further comprising bending each lateral wing in the forward direction relative to a remainder of the upper portion.

In some arrangements, the step of bending at least one of at least the portion of the upper portion and at least the portion of the neck forward relative to the lower base portion may include introducing a curvature along a majority of the upper portion and along at least a portion of the neck.

In some arrangements, the step of bending at least one of at least the portion of the upper portion and at least the portion of the neck forward relative to the lower base portion may include introducing a bend on at least the portion of the upper portion or at least the portion of the neck, the remainder of the neck and upper portion on both the top and bottom of the bend are linear.

In some arrangements, the method may include a step of creating at least one slot on an upper edge of each tab, the upper edge being opposed to the lower edge of the respective tab.

In some arrangements, the method may include a step of creating at least one slot on at least one of the lateral middle edges.

In another aspect, a method of intubating a patient may comprise observing the patient through a transparent barrier extending from a bed on which the patient lies and over the patient, and reaching around the barrier to access the patient and/or manipulate a tube.

In some arrangements, the barrier may include a lower base portion extending between two lower lateral edges, and a first tab and a second tab extending laterally from the two lower lateral edges of the lower base portion, each tab including a lower bottom edge including at least one slot extending upward from the lower bottom edge, an upper portion extending between two upper lateral edges, and a neck joining the lower portion and the upper portion, the neck extending between two middle lateral edges, a distance between the middle lateral edges being less than a distance between the two lower lateral edges and a distance between the two upper lateral edges, wherein the reaching step includes reaching around at least one of the middle lateral edges of the neck to access the patient.

In some arrangements, at least one of the lateral middle edges may include at least one slot, the method further comprising the step of positioning the tube within the at least one slot.

In another aspect, a barrier may comprise a lower base portion extending between two lower lateral edges, and a first tab and a second tab extending from the two lower lateral edges of the lower base portion, each tab including a lower bottom edge having an engagement feature, an upper portion extending between two upper lateral edges, and a neck joining the lower portion and the upper portion, the neck extending between two middle lateral edges, a distance between the middle lateral edges being less than a distance between the two lower lateral edges and a distance between the two upper lateral edges.

In some arrangements, the engagement feature may include at least one slot extending upward from the lower bottom edge.

In some arrangements, at least a portion of each of the middle lateral edges may be concave.

In some arrangements, each tab may extend in a forward direction relative to a remainder of the lower base portion.

In some arrangements, at least one of at least a portion of the upper portion and at least a portion of the neck may extend in a forward direction relative to the lower base portion.

In some arrangements, at least one of the lateral middle edges may include at least one slot.

In some arrangements, each tab may include an upper edge opposed to the lower edge of the respective tab, the upper edge of at least one tab includes at least one slot.

In some arrangements, the upper portion may include lateral wing portions extending from each upper lateral edge inwardly towards a middle area of the upper portion, each lateral wing portion extending in a forward direction relative to a remainder of the upper portion.

In some arrangements, at least one of at least a portion of the upper portion and at least a portion of the neck may extend in a forward direction relative to the lower base portion.

In some arrangements, a majority of the upper portion and at least a portion of the neck may include a curvature such that a top portion of the upper portion extends in the forward direction more than a bottom portion of the upper portion or the neck.

In some arrangements, at least a portion of the upper portion or at least the portion of the neck may include a bend, and the remainder of the neck and upper portion on both the top and bottom of the bend are linear.

BRIEF DESCRIPTION OF THE DRAWINGS

FIGS. 2B-2D are a back elevation view, side elevation view, and a top plan view, respectively, of the barrier of FIG. 2A, the side elevation view of the other side of the barrier is a mirror image of FIG. 2C.

FIGS. 3B-3D are a back elevation view, side elevation view, and a top plan view, respectively, of the barrier of FIG. 3A, the side elevation view of the other side of the barrier is a mirror image of FIG. 3C.

FIGS. 9B-9D are a back elevation view, side elevation view, and a top plan view, respectively, of the barrier of FIG. 9A, the side elevation view of the other side of the barrier is a mirror image of FIG. 9C.

DETAILED DESCRIPTION

The various embodiments of barriers, methods of use, methods of manufacture, and use with a patient and a hospital bed discussed herein are examples only and the present disclosure is not limited in any way. For instance, while various panels and portions of the barrier are discussed separately, the barrier may be monolithic, though a barrier of modular construction is also envisioned where any or all of the panels can be separate pieces that combine to form the barrier. In another example, while the barriers disclosed herein are used with a bed in an operating room, the barriers may also be used in other healthcare settings, such as a normal hospital bed, an ICU bed, and may even be incorporated onto a standalone structure that can be positioned near a bed and/or a patient. The barriers of the present disclosure are generally discussed in the context of intubation, but may be used during any procedure where aerosols or other potentially hazardous substances may exit the patient's airways.

Figure 1A:
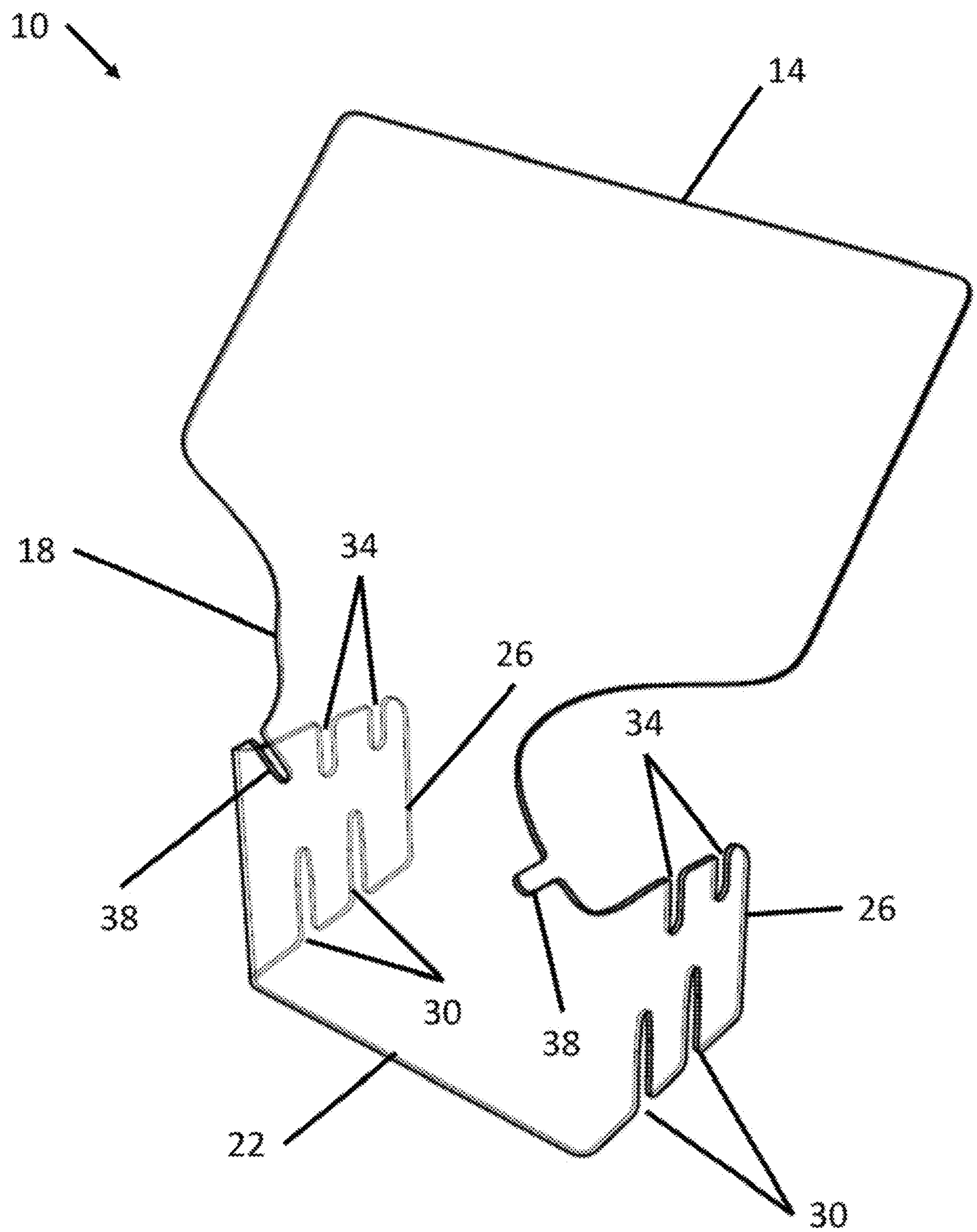
FIG. 1A is an oblique perspective view of a barrier according to an aspect of the disclosure.
Figure 1B:
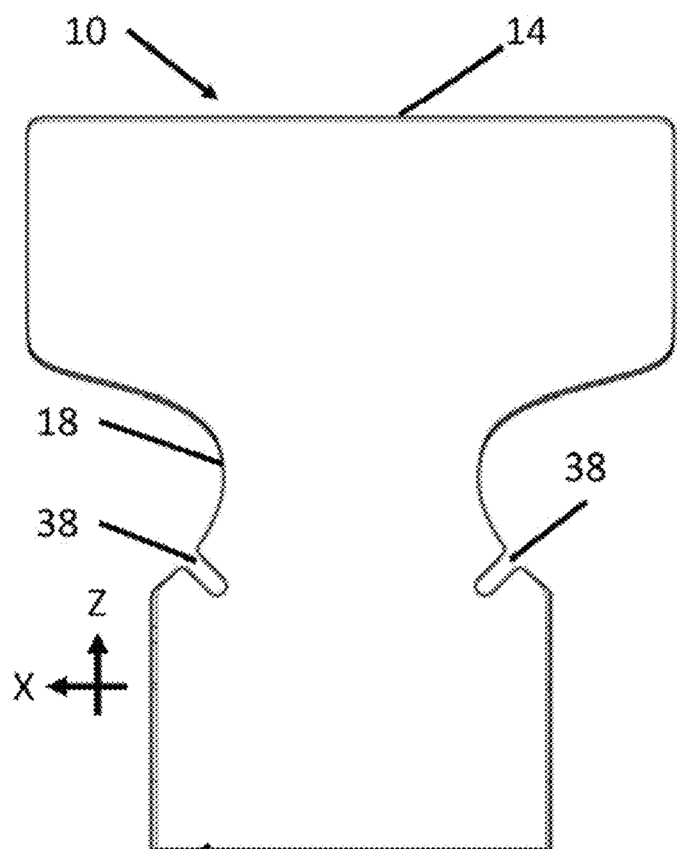
FIGS. 1B-1D are a back elevation view, side elevation view, and a top plan view, respectively, of the barrier of FIG. 1A, the side elevation view of the other side of the barrier is a mirror image of FIG. 1C.
Figure 1C:
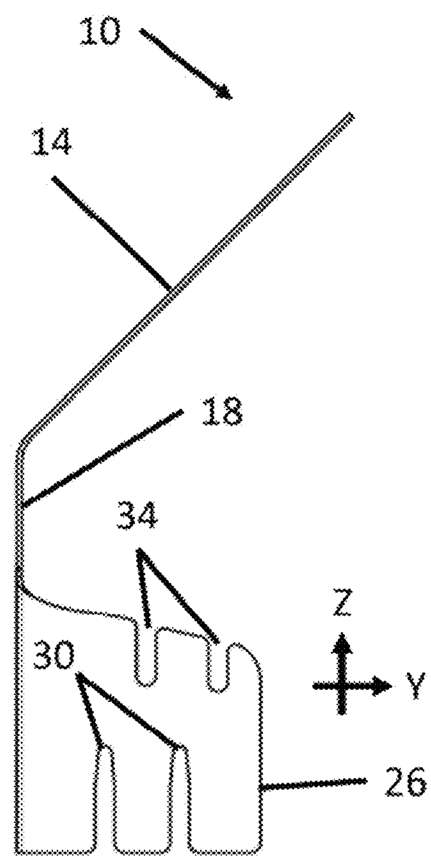
Figure 1D:
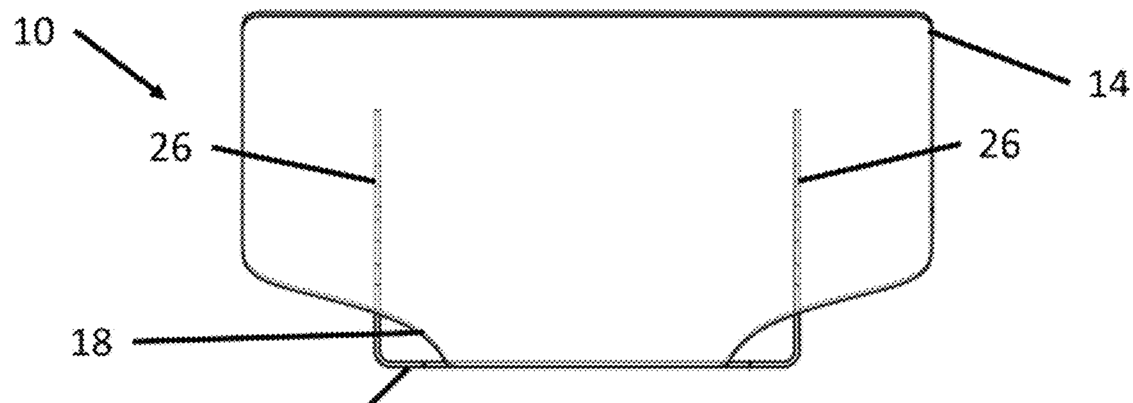
Figure 1E:
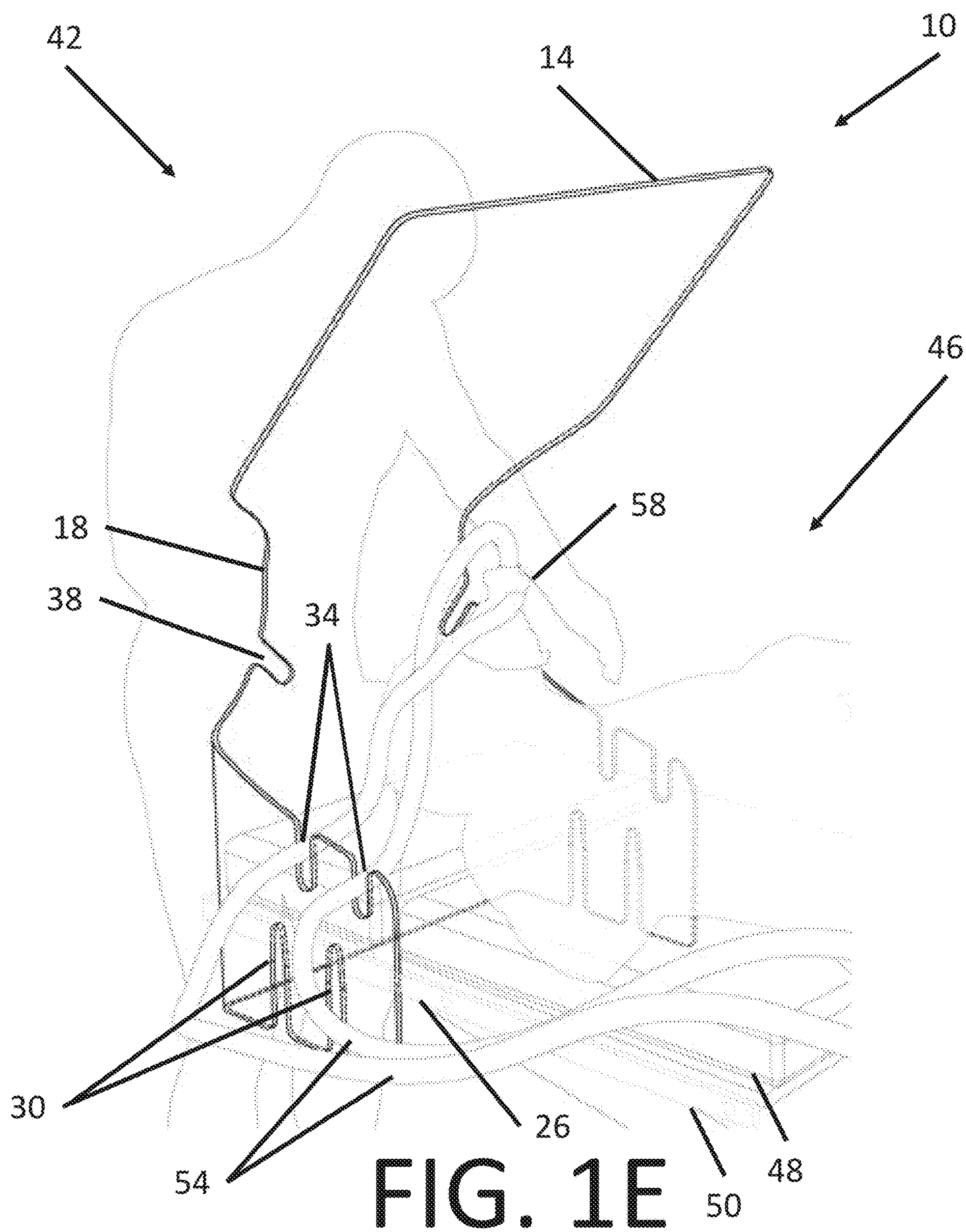
FIG. 1E illustrates an exemplary use case for the barrier of FIG. 1A.

An embodiment of a barrier 10 for use in an operating room is shown from various perspectives in FIGS. 1A-D, and in an exemplary use case in FIG. 1E. The barrier 10 includes a shield 14 connected to a back panel 22 by a neck 18. The back panel 22 extends along a plane defined on both a lateral axis X and vertical axis Z. These various panels and shield of the barrier 10 may form a monolithic barrier or alternatively one or more could be separate pieces connectable to one another to form a modular structure. The shield 14 is also planar, and extends at an oblique angle from the back panel 22 with a forward component along a longitudinal axis Y. In the illustrated example, the shield 14 extends at about a 45° angle relative to the back panel 22. A bend in the neck 18 curves in transition between respective planes of the shield 14 and back panel 22, thus defining an arc subtending about 135°. In some alternative arrangements, the bend has a larger or smaller radius than that shown in the illustrated example. In further alternatives, the bend is located above or below the neck 18, or through the neck 18 and/or below the neck 18. However, the shield 14 may extend at an angle of anywhere from 0° to 90° relative to the back panel 22, corresponding to angles subtended by the neck of 180° to 90°. In this illustrated example, the shield 10 is about 710 mm across on the lateral axis X and about 450 mm long.

Two parallel side panels 26 extend forward from and perpendicular to the back panel 22 on planes defined on the longitudinal axis Y and vertical axis Z. The side panels 26 may be spaced laterally apart by a distance that is slightly greater than a width of a mattress 48 of a hospital bed so that the side panels 26 may extend along either side of the mattress while the back panel 22 is situated along a head of the mattress 48 as shown in FIG. 1E. In the illustrated example, the back panel 22 is no wider laterally than the distance between the side panels 26 so that the back panel 22 and side panels may sit within a frame 50 around the mattress. In a specific example suitable for use with Steris 4085 hospital beds, the lateral distance between the side panels 26 is about 529 mm, and the side panels 26 are about 319 mm long along the longitudinal axis Y. However, barriers 10 may be constructed with any distance between the side panels 26 as appropriate for a given hospital bed.

The shield 14 may be equal to or laterally wider than the distance between the side panels 26 so as to catch or deflect aerosols emitted from the airways of a patient 46 across a broad angular range. As illustrated, shield 14 is laterally wider than the distance between the side panels 26 in order to increase the amount of protection to the worker 42. As illustrated in FIG. 1E, the shield 14 thereby provides a space behind the head of the bed where worker 42, such as a physician or nurse, may stand whereby the barrier will interfere with a direct pathway for aerosols from the patient to the worker, thereby decreasing the risk that the aerosols will directly contact the work or reach the worker's 42 own airways.

The neck 18 is laterally narrower than the shield 14 and the back panel 22, enabling the worker 42 to reach around the neck 18 to access the patient 46 while the worker's 42 face remains on an opposite side of the shield 14 from the patient 46. Because the shield 14 is transparent, the worker 42 may observe the patient 46 through the shield 14 while reaching around the neck 18.

Referring again to FIGS. 1A and 1C, one or both side panels 26 can include at least one mounting slot 30, which as illustrated extend upward from lower edges of the side panels 26. The mounting slots 30 are spaced and dimensioned to slide over, using the exemplary bed of FIG. 1E, posts that extend inward from the outer perimeter of the frame 50. In the illustrated example, the mounting slots are about 140 mm deep and about 25 mm wide at the lower edge of the side panels 26, and taper to end in semicircles about 17 mm in diameter. The taper enables the mounting slots 30 to slide easily over posts of less than 25 mm in diameter, then settle tightly onto the posts to prevent the barrier 10 from moving longitudinally when it is seated within the frame 50. Moreover, the slots 30 are located on the side panels 26 relative to a center of gravity of the barrier 10 to inhibit the barrier 10 from tilting when supported within the mounting slots 30. The mounting slots 30 therefore enable the barrier 10 to be stably positioned at the head of the bed as shown in FIG. 1E by sliding the mounting slots 30 onto the posts of the frame 50. Again, the distance between slots and other dimensions may vary as appropriate for any intended model of hospital bed. Of course, alternative such engagement features than slots 30, or in addition to at least one slot 30, may also be included on the barrier 10 depending on the type of connection needed. For instance, if the bed frame instead has one or more slots in the frame, the barrier 10 may instead include one or more prongs for insertion into the slot(s) of the bed frame. Thus, the mounting slots 30 are one example of an engagement feature that could be used to retain barriers according to the present disclosure to a hospital bed. However, other engagement features, such as prongs, tabs, clamps, hooks, projections with mechanical adhesives, such as microsuction tape, hook patches for hook and loop adhesion (like that used in Velcro® products), draping adhesion (like that used in Geckskin® products), or the like, for engagement to the bed, a pillow, and/or sheets, may be implemented with barriers according to any arrangement of this disclosure. Further, rather than a hospital bed, the barrier may instead be configured to engage another structure such as a podium, a hospital cart (e.g., to make the barrier a portable structure capable of being moved around an operating room or between rooms), a chair, or the like.

Additionally, as illustrated in FIGS. 1A and 1C, one or both of side panels 26 may also include one or more retaining slots 34 which extend downward from upper edges of the side panels 26. The retaining slots 34 may be used for holding or positioning various devices. For example, as shown in FIG. 1E, the retaining slots 34 are used to retain tubes 54 from a ventilator, thereby isolating a mask 58 from the weight of the tubes 54. Similarly, as illustrated in FIGS. 1A and 1B, one or more neck slots 38 may be positioned on either or both concave surfaces of the neck 18 and extend downward and laterally inward into the neck 18. The retaining slots 34 and neck slots 38, if and where present, can be used in any way convenient for the worker 42, and may vary in placement, number, and orientation in alternative arrangements. In the illustrated example, the retaining slots 34 and neck slots 38 are both about 25 mm wide.

Figure 1F:
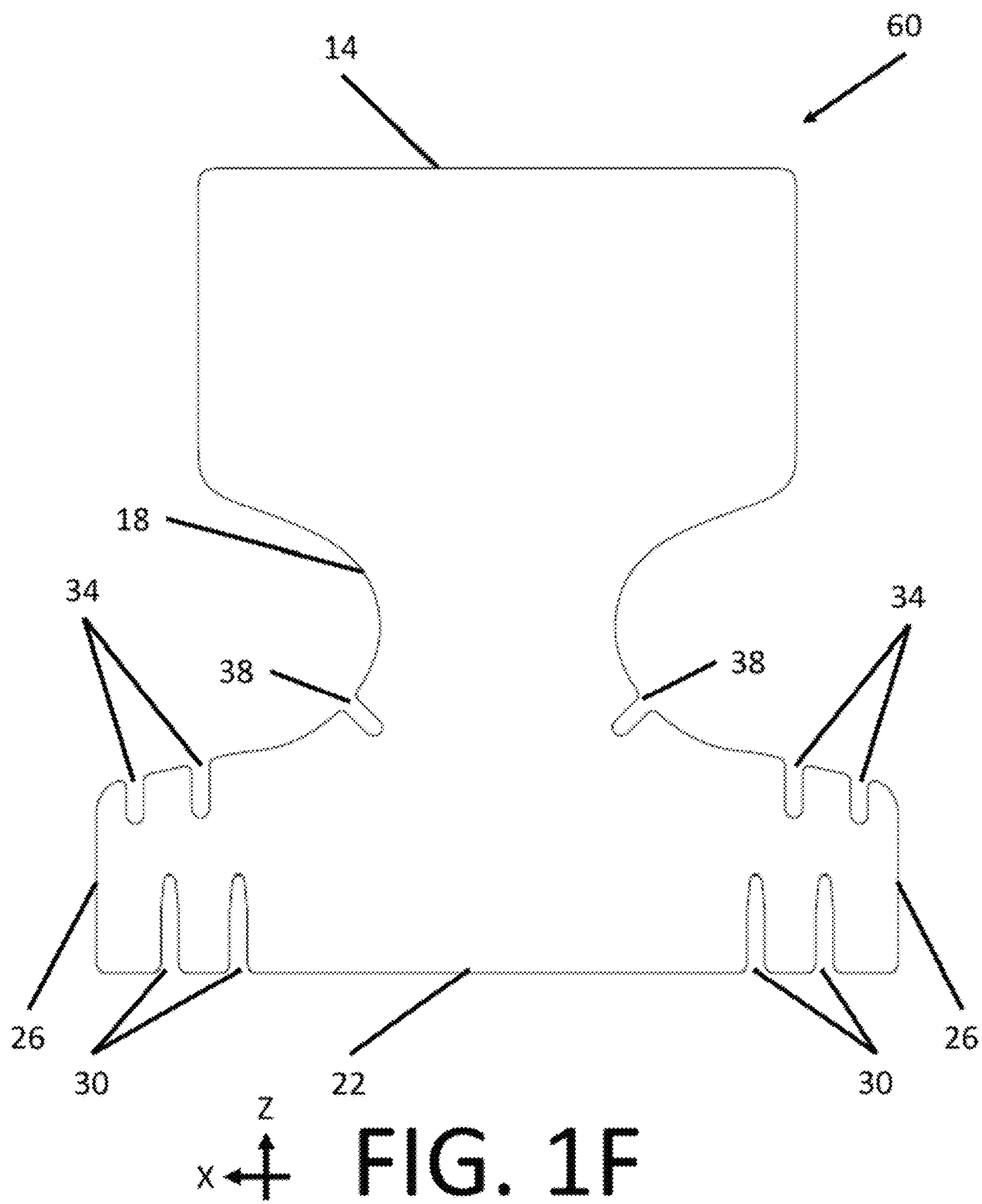
FIG. 1F is a plan view of a sheet as may be produced during an exemplary method of manufacturing the barrier of FIG. 1A.

FIG. 1F illustrates a shaped sheet 60 produced at a step of an exemplary method for manufacturing the barrier 10. The sheet 60 includes the shield 14, neck 18, mounting slots 30, retaining slots 34, neck slots 38, and a precursor to the back panel 22 and side panels 26 in the form of a lower base portion that extends laterally wider than the shield 14. In the illustrated example, the lower base portion is about 149 mm across along the lateral axis X, and a total height of the sheet along the vertical axis Z is about 1151 mm. The shaped sheet 60 may be produced by any suitable process such as, for example, blanking from a larger sheet of transparent material, cutting feature by feature, or injection molding. The sheet 60 is finished into the barrier 10 by bending the lower base portion to turn the side panels 26 forward until they are aligned with the longitudinal axis Y and perpendicular to the back panel 22, and by bending the neck 18 forward until the shield 14 extends at a desired angle relative to the back panel 22. The sheet 60 may be of any thickness that is both thick enough for repeated use without breaking and thin enough for a chosen forming method and to fit between the frame 50 and mattress 48, such as equal to or about 6 mm thick.

Sheet 60 may be of any suitable material for use as a barrier, though considerations such as the weight of barrier 10, relative to its strength must be considered. For instance, the barrier 10 should be light enough such that one or two people can lift and position it on the bed, or other structure, however, barrier 10 must also be strong enough such that it can withstand repeated uses, be generally scratch resistant, and be capable of handling sanitization procedures, including the use of harsh chemicals. Further, barrier 10 should be strong enough such that if a user accidentally leans on it, it would not break and injure the patient. Generally, the preferred material is polycarbonate (Lexan®) or poly(methyl methacrylate) (Plexiglass or Plexiglas®), although other materials such as polyethylene terephthalate glycol (Vivak®) are envisioned FIGS. 2A-2D illustrate a barrier 110 according to another embodiment. Like numerals refer to like elements (i.e., the back panel 122 and side panels 126 are generally alike to the back panel 22 and side panels 126 shown in FIGS. 1A-1E) unless otherwise noted. The barrier 110 differs from the barrier 10 of FIGS. 1A-1E in that the shield 114 includes two wings 162 extending forward from opposite lateral edges of the shield 114 at opposite, oblique angles. The barrier 110 may be formed according to the same methods as described with regard to FIG. 1F, with an additional step of bending lateral ends of the shield 114 forward to create the wings 162. Because the wings 162 extend forward, they extend around the patient's 46 head, and therefore may deflect aerosols from the patient's 46 airways a comparable angular range to those deflected by the shield 14 of FIGS. 1A-1E. However, lateral outer edges of the wings 162 are closer together than laterally opposite edges of the panel 14 of FIGS. 1A-1E, meaning the barrier 110 may have similar efficacy to the barrier 10 with a somewhat more compact design and enabling the worker 42 to safely observe the patient 46 from additional perspectives than simply directly behind shield 14, such as from more of a lateral direction, i.e., from directly behind the wings 162. In the illustrated example, the wings 162 extend at an angle that is about 145° from the perspective of FIG. 2D, and upper edges of the wings 162 are about 99 mm long.

FIGS. 3A-3D illustrate a barrier 21 according to another alternative arrangement. Like numerals refer to like elements (i.e., the back panel 222 and side panels 226 are generally alike to the back panel 22 and side panels 26 shown in FIGS. 1A-1E) unless otherwise noted. The barrier 210 differs from the barrier 10 of FIGS. 1A-1E in that the shield 114 curves arcuately forward. Further, the neck 218 may be coplanar with the back panel 222. The barrier 210 may be formed according to the same methods as described with regard to FIG. 1F, except with a step of bending the shield 214 to produce the arcuate shape instead of bending the neck 18 while keeping the shield 14 linear as in FIG. 1A. Similar to the wings 162, the curved shield 214 extends around the patient's 46 head, which may provide additional perspectives for the worker viewing the patient as well as providing comparable functionality to that of the barrier 10 of FIGS. 1A-1E, but with a slightly more compact shape.

Any use of approximating terms such as "about" or "approximately" in the foregoing description with regard to a quantity should be interpreted to mean that the specific quantity stated and all quantities within ±15% of the stated quantity are contemplated. Further, it should be understood that the dimensions, angles, and proportions illustrated and described are merely exemplary, and alternative arrangements to those shown may vary to accommodate a variety of parameters including the model of hospital bed with which a barrier may be used, an intended medical procedure, and storage considerations.

Figure 2A:
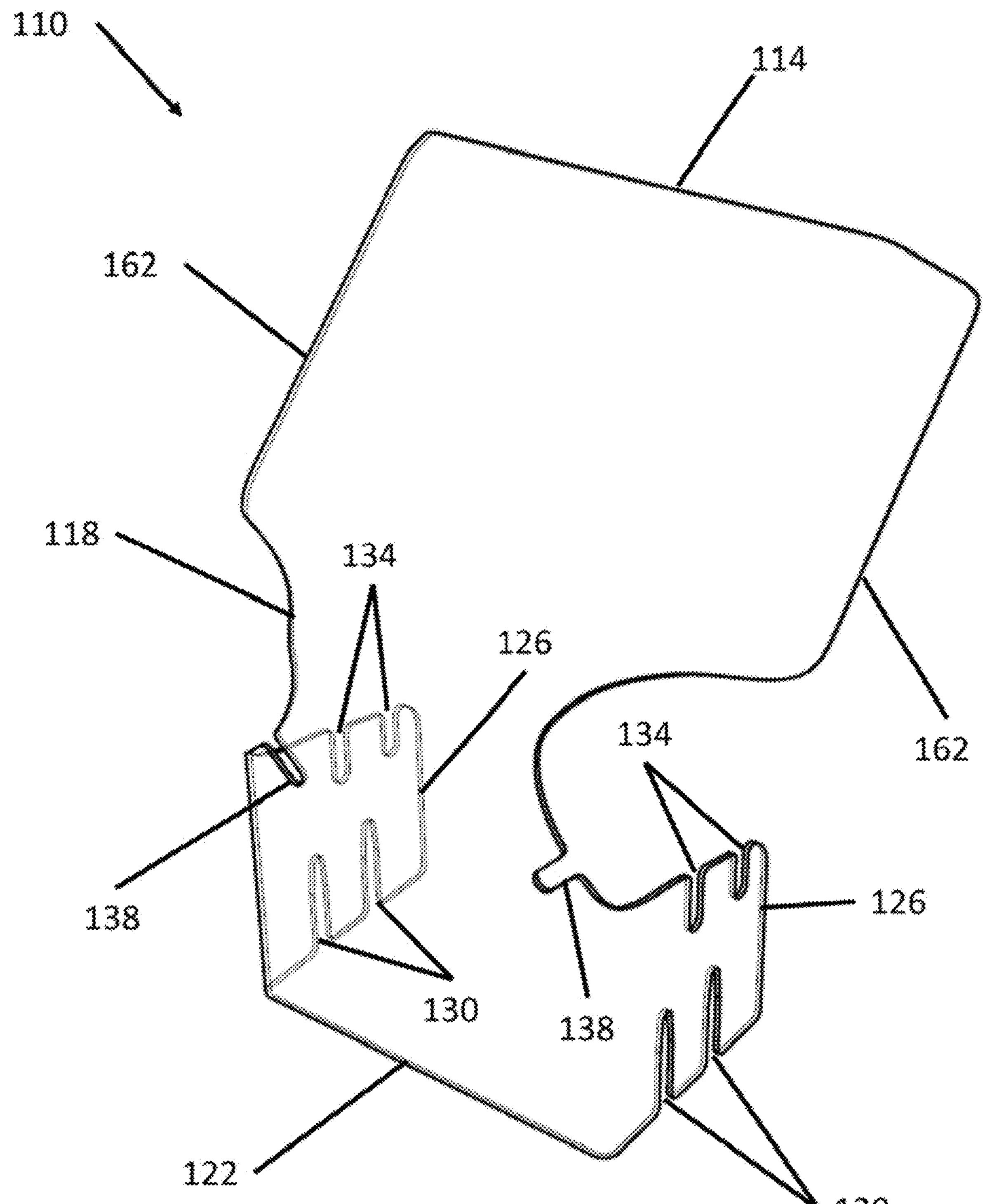
FIG. 2A is an oblique perspective view of a barrier according to an aspect of the disclosure.
Figure 3A:
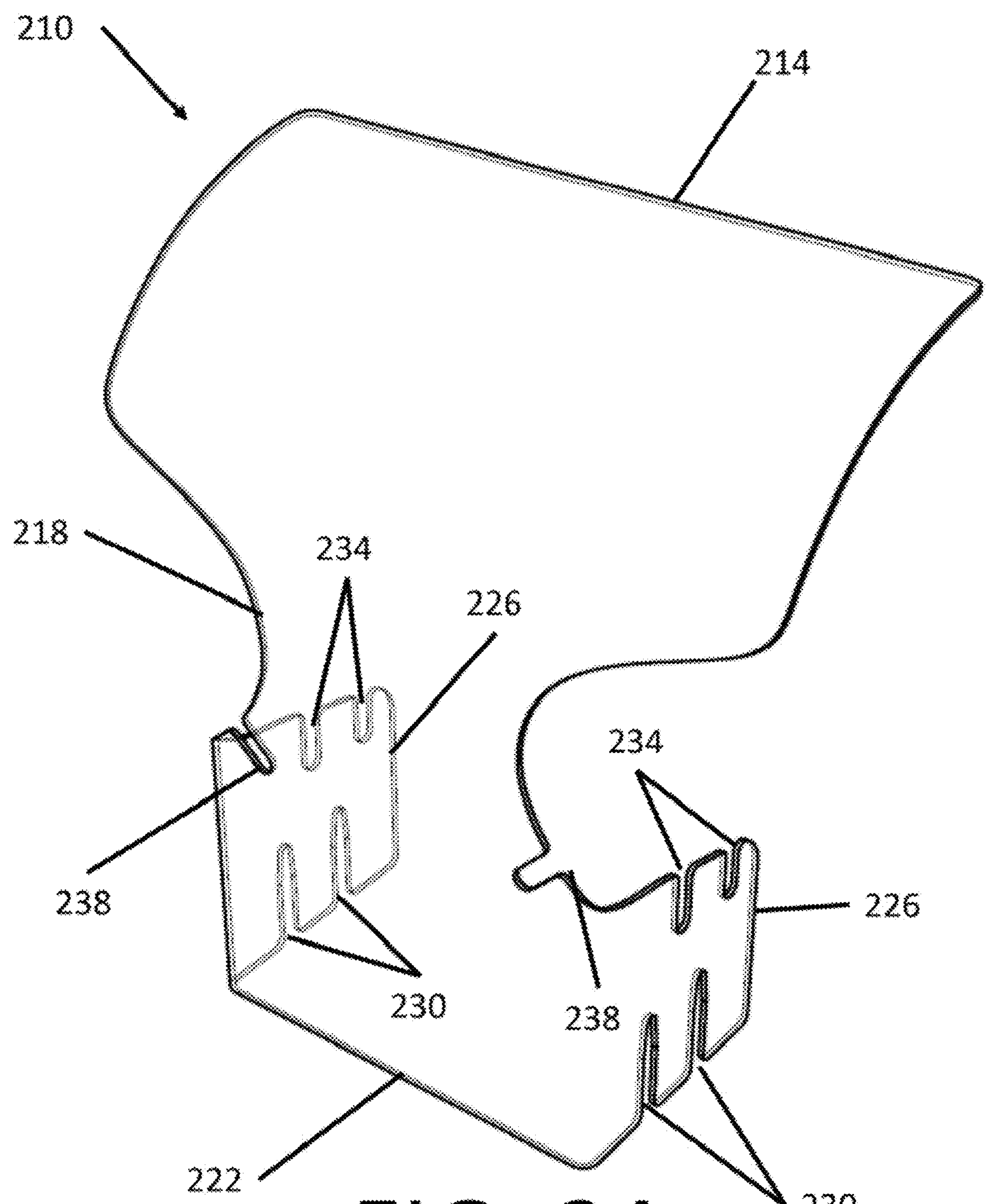
FIG. 3A is an oblique perspective view of a barrier according to an aspect of the disclosure.
Figure 4A:
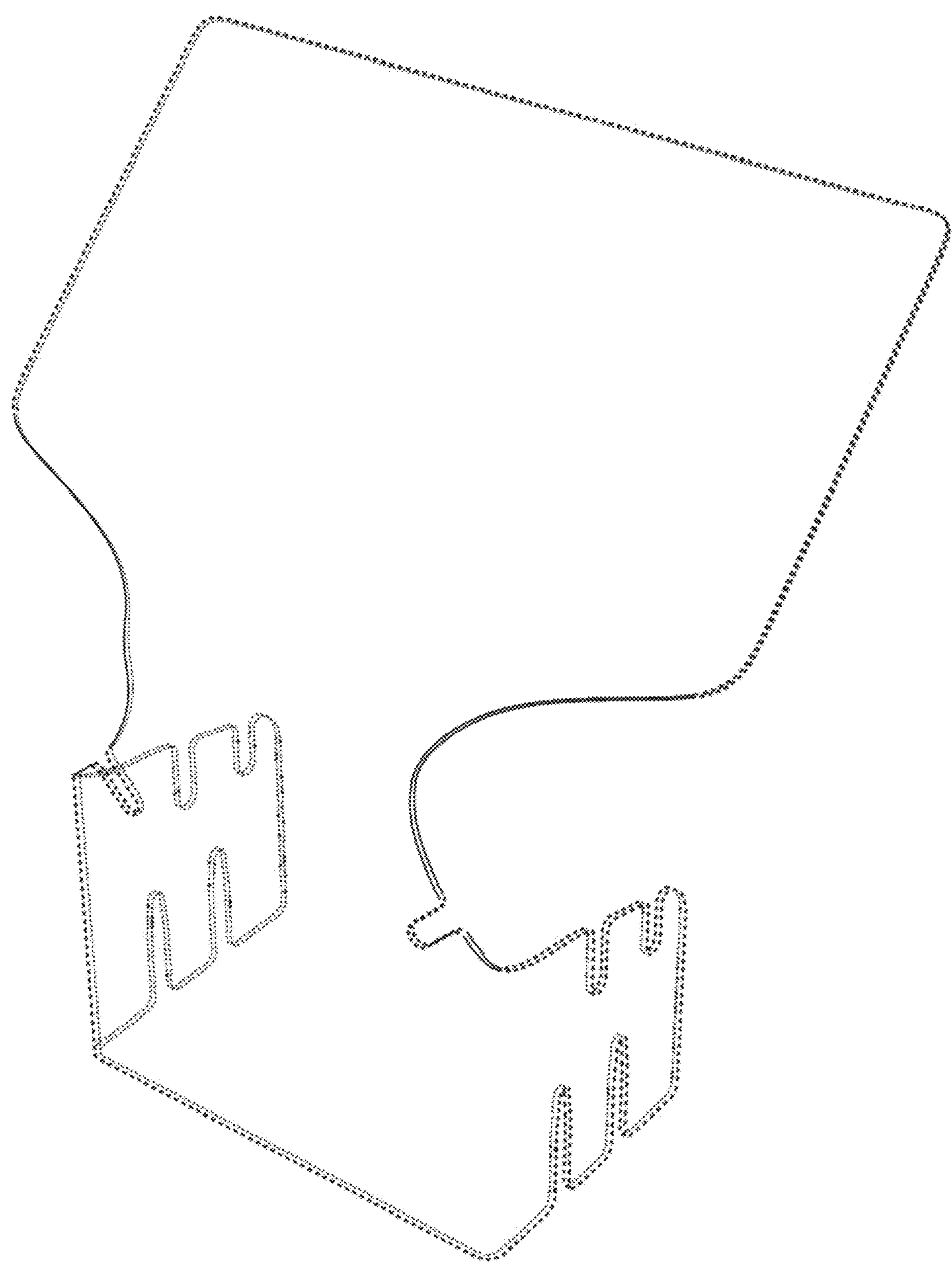
FIGS. 4A-6B are oblique perspective views of barriers according to other aspects of the disclosure.
Figure 4B:
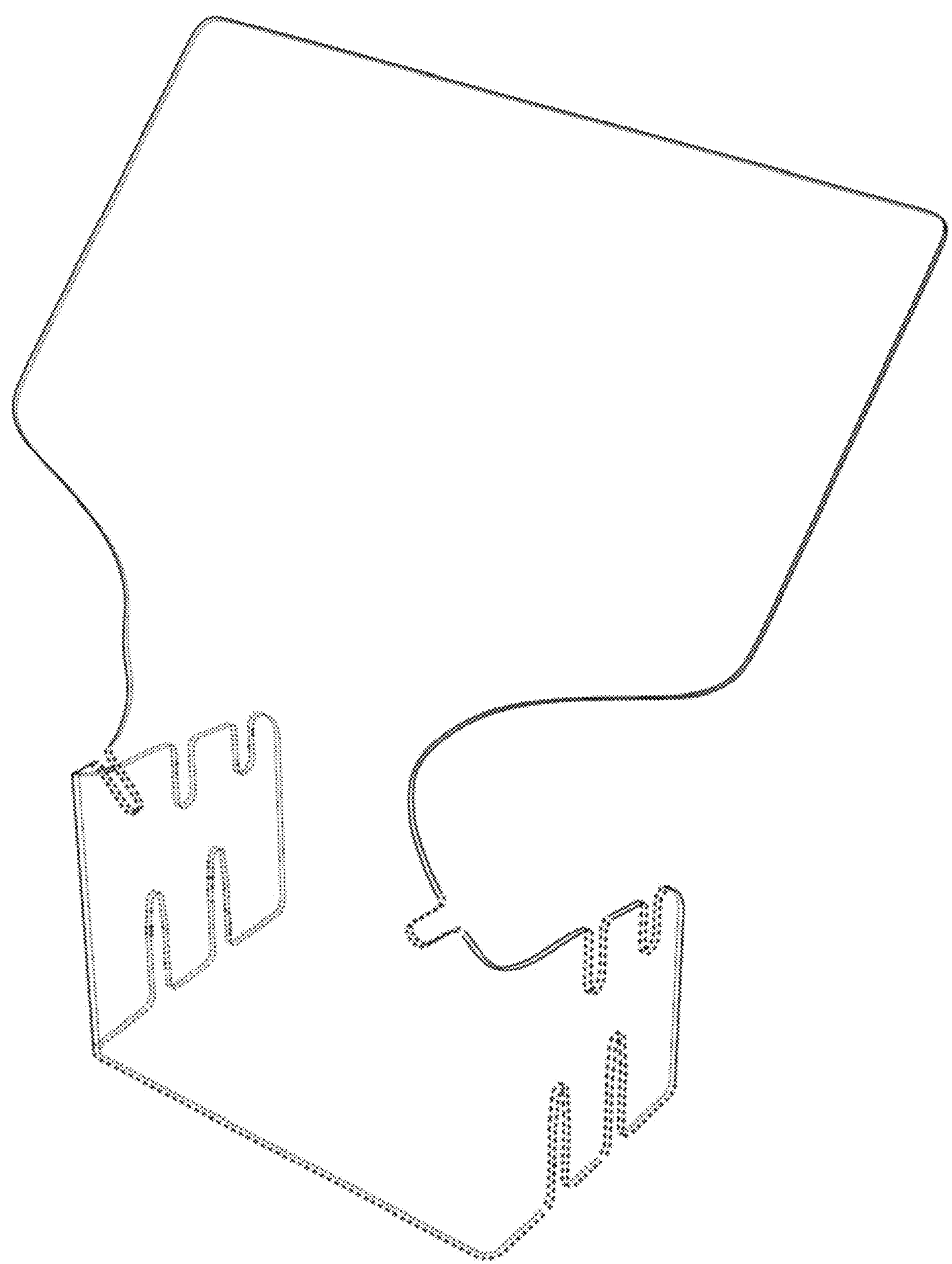
Figure 5A:
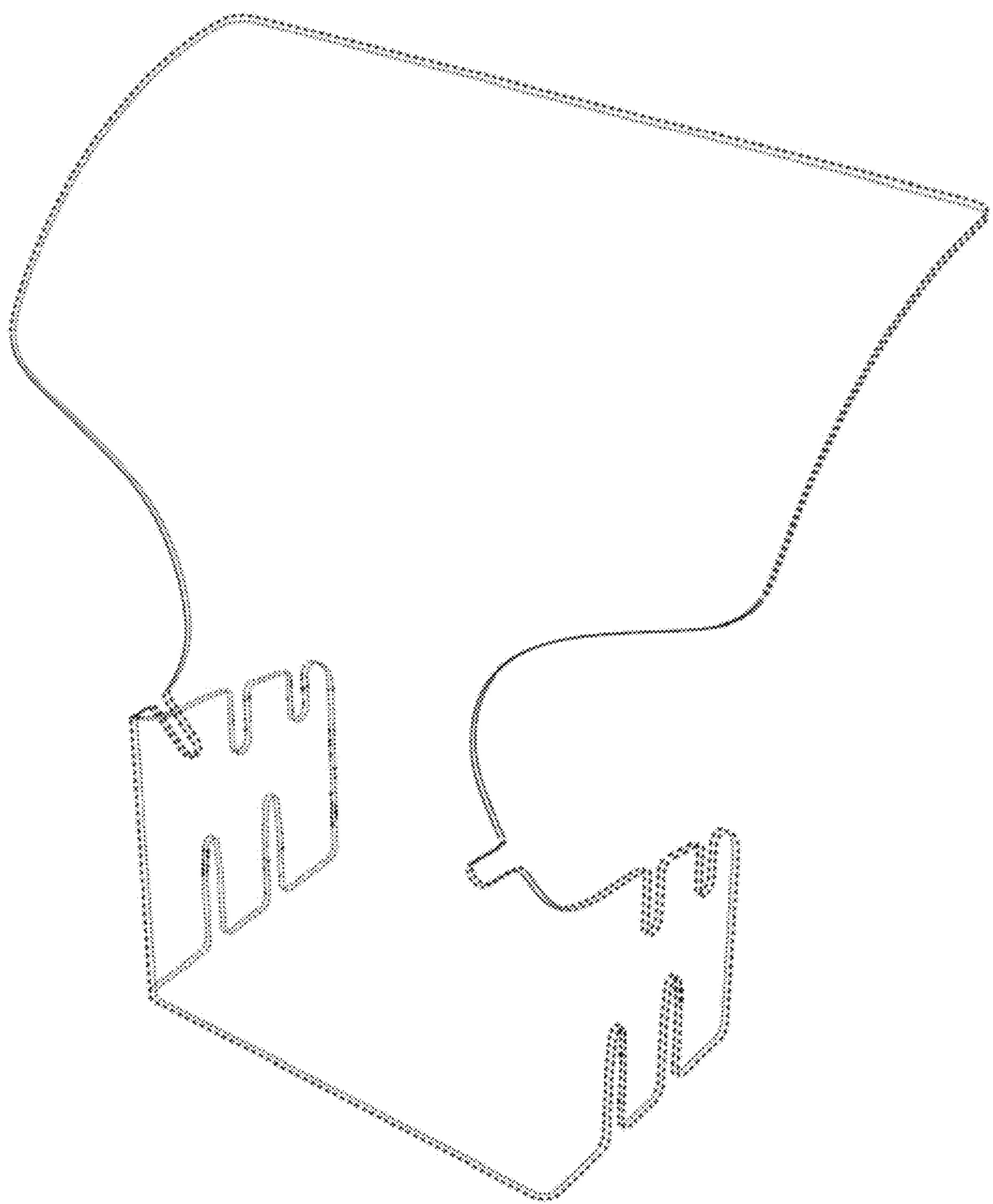
Figure 5B:
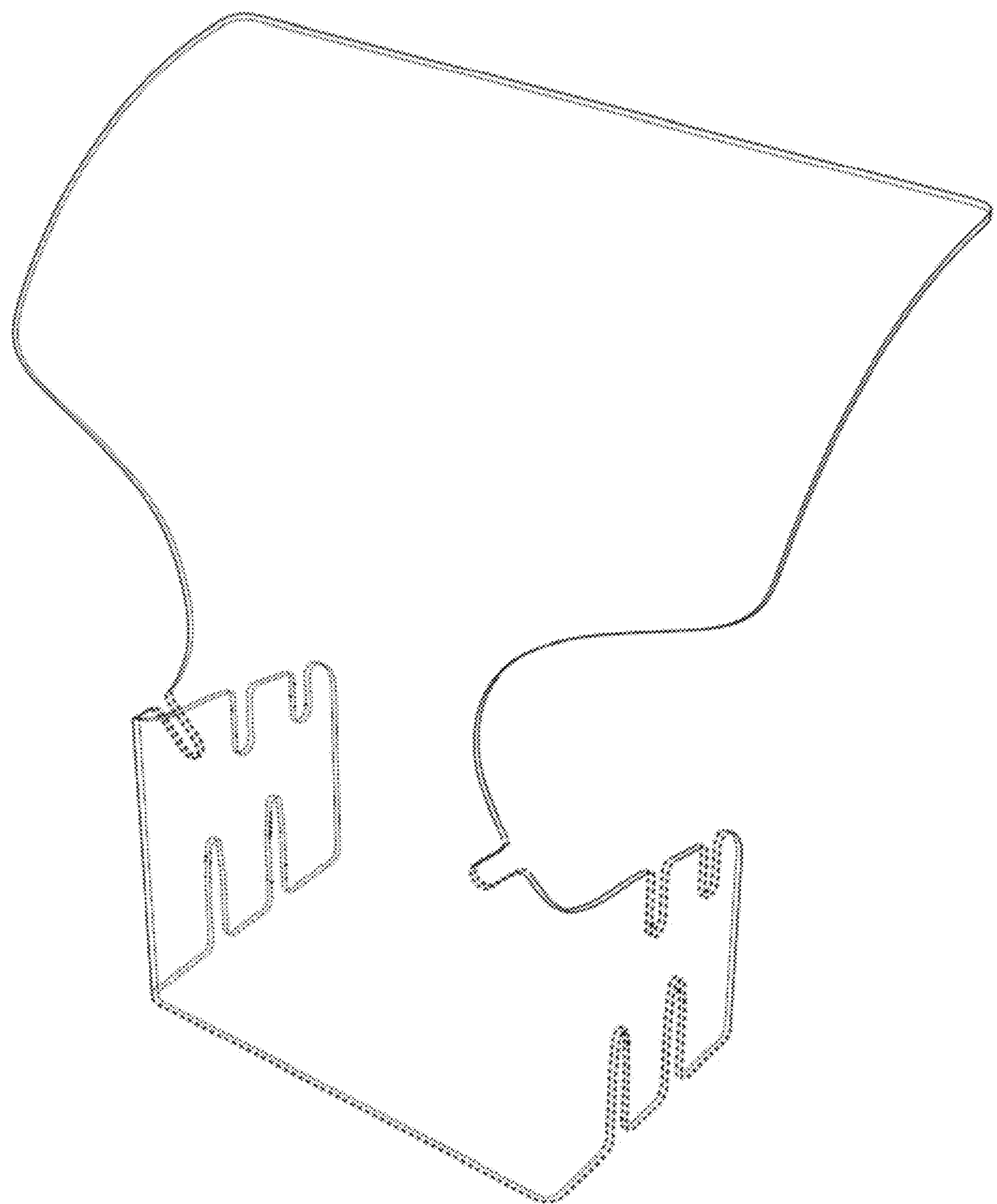
Figure 6A:
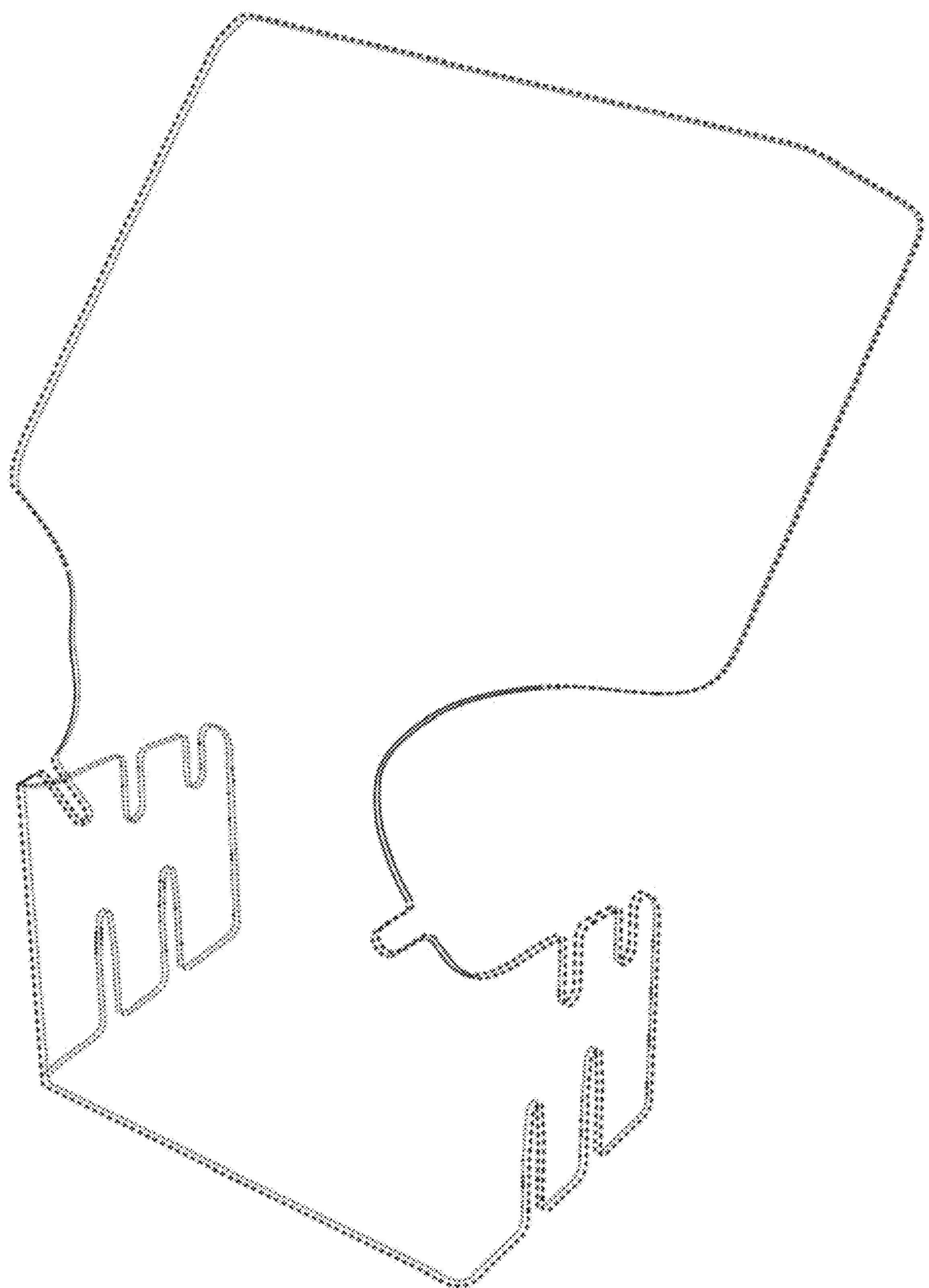
Figure 6B:
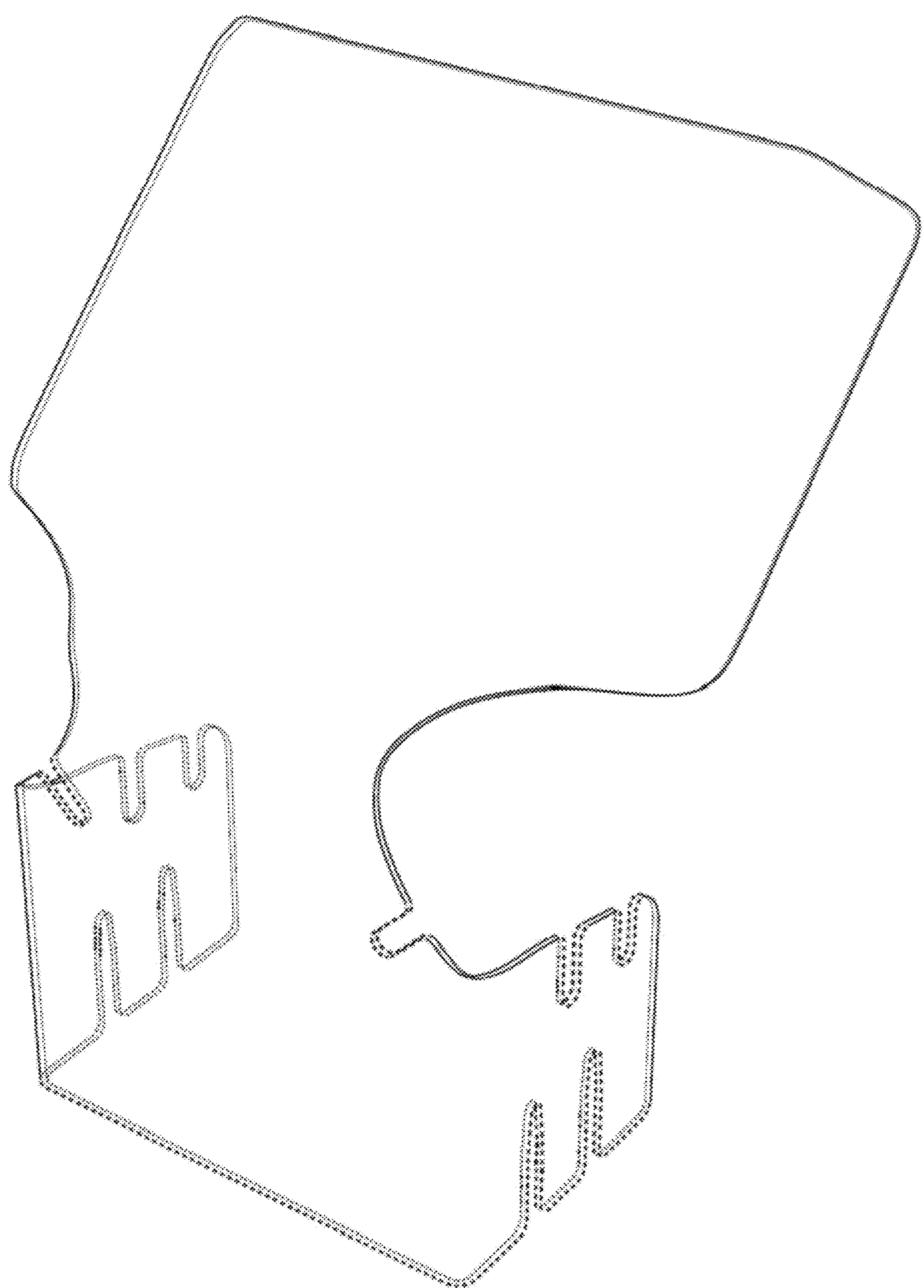
Figure 7A:
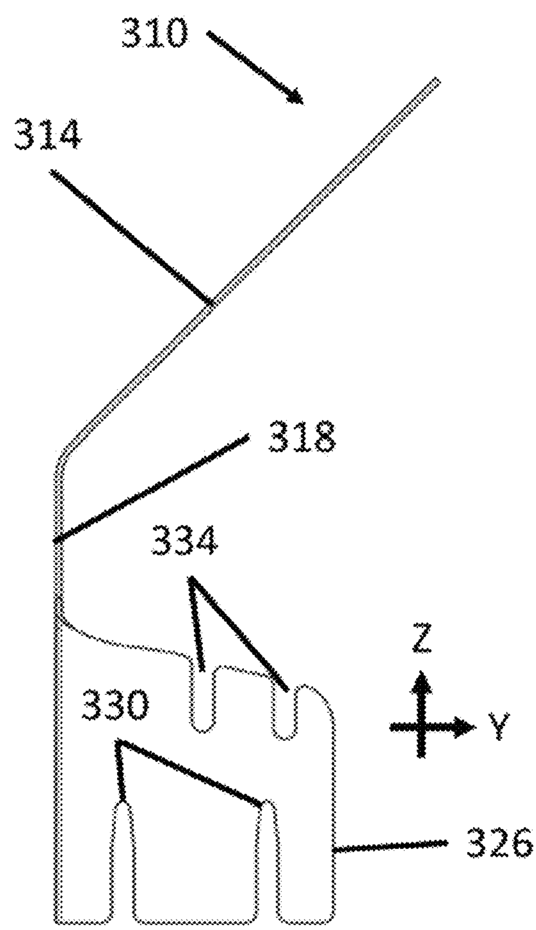
FIGS. 7A and 7B are side elevation views of barriers according to aspects of the disclosure.
Figure 7B:
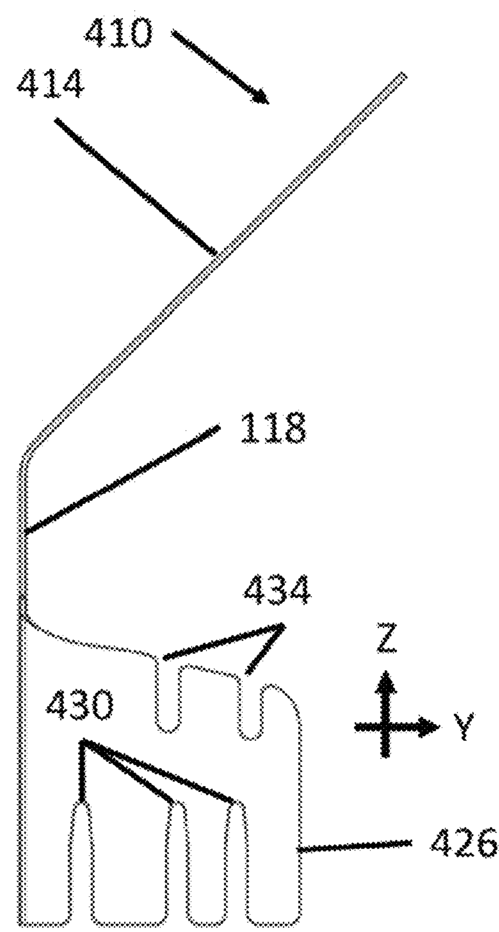
Figures 8A, 8B:
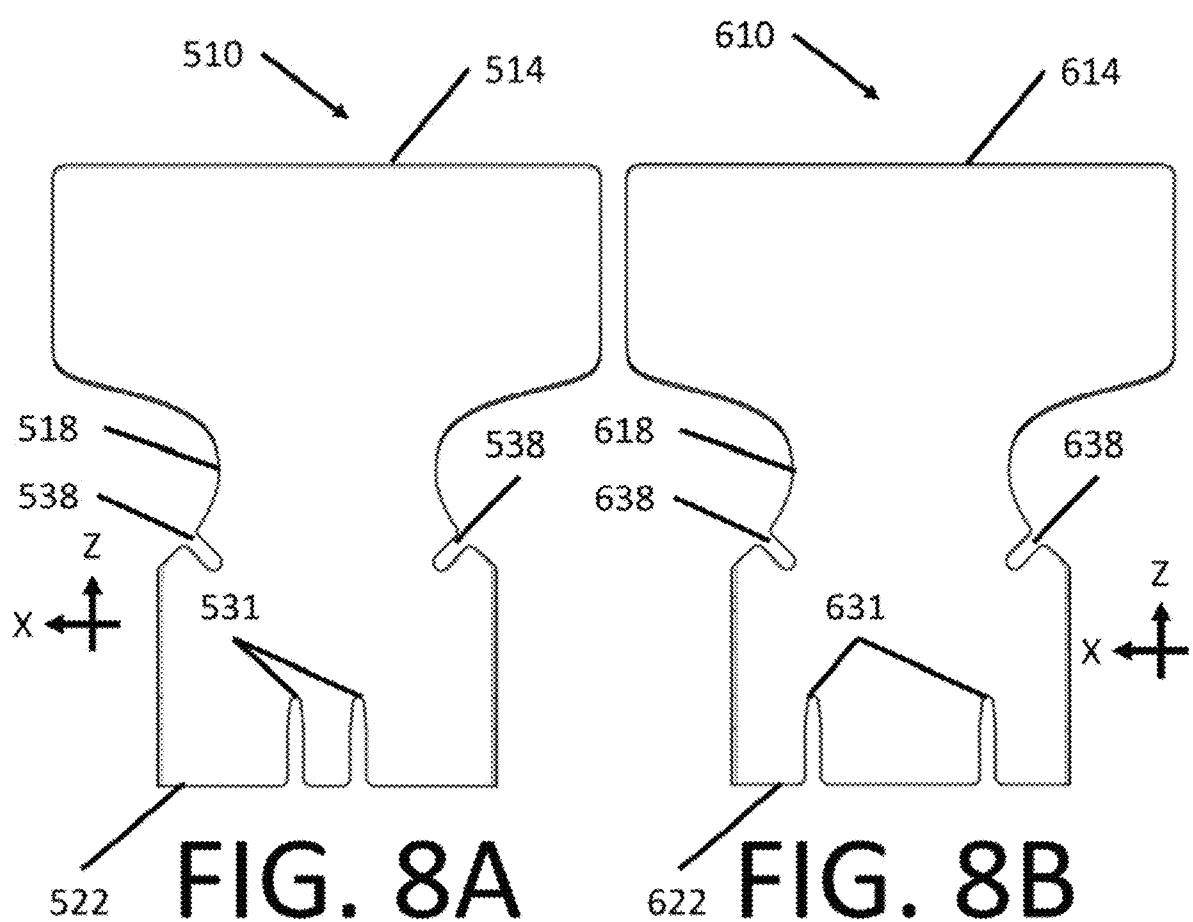
FIGS. 8A and 8B are back elevation views of barriers according to aspects of the disclosure.

FIGS. 4A and 4B each illustrate further alternative barrier embodiments according to the present disclosure. In both FIGS. 4A and 4B, solid lines indicate portions of the design, whereas dashed lines indicate environmental or merely exemplary details that are not part of the design. For instance, in FIG. 4A, which is the same barrier as barrier 10 of FIGS. 1A-1E (where the other side not shown in FIG. 1C is a mirror image of FIG. 1C), the concave portions defining the neck are illustrated in solid line, while the remainder of the barrier is illustrated in dotted line, such that the neck are a constant portion of the design while the remaining aspects of the barrier can be altered as desired. In the other example of FIG. 4B, which is the same barrier as barrier 10 of FIGS. 1A-1E (where the other side not shown in FIG. 1C is a mirror image of FIG. 1C), the concave portions defining the neck, the shield 14, and various edges of the back panel 22 and side panels 26 are illustrated in solid line, while the lower edges of the side panels and back panel, and the various slots on the neck and side panels are illustrated in dotted line, such that the neck, shield, back panel and side panels generally are a constant portion of the design while the various slots can be present, not present, moved, or altered as desired. FIGS. 5A and 5B similarly show the barrier 110 of FIGS. 2A-2D (where the other side not shown in FIG. 2C is a mirror image of FIG. 2C), and FIGS. 6A and 6B similarly show the barrier 210 of FIGS. 3A-3D (where the other side not shown in FIG. 3C is a mirror image of FIG. 3C), with certain portions shown in dotted lines and therefore excluded from the design. In FIGS. 5A and 6A, the concave portions defining the neck are illustrated in solid line, while the remainder of the barrier is in dotted line, and in FIGS. 5B and 6B, the shield and various edges of the back panel and side panels are in solid line, while the lower edges of the side panels and back panel, and the slots are in dashed lines, with dashed lines in all instances indicating elements that are excluded from the design and may thus be omitted, reshaped, or repositioned.

FIGS. 7A-8B illustrate barriers 310, 410, 510, 610 according to further alternative arrangements. The barrier 310 of FIG. 7A includes two mounting slots 330 on lower edges of side panels 326 that are spaced further apart than the two mounting slots 30 per side panel 26 of the barrier 10 of FIGS. 1A-1E. The barrier 410 of FIG. 7B includes three mounting slots 430 per side panel 426 in contrast to the two mounting slots 30 per side panel 26 of the barrier 10 of FIGS. 1A-1E. The barriers 510, 610 of FIGS. 8A and 8B include two additional mounting slots 531, 631 extending upward from lowermost edge of respective back panels 522, 622, with the additional mounting slots 631 of FIG. 8B being spaced further apart than the additional mounting slots 531 of FIG. 8A. Other elements of the barriers 310, 410, 510, 610 of FIGS. 7A-8B correspond to the elements of the barrier 10 of FIGS. 1A-1E, and are therefore not enumerated or further detailed here. However, any of the features shown in FIGS. 7A-8B may be implemented in any combination in any of the barriers 10, 110, 210 shown in FIGS. 1A-3D. Moreover, mounting slots or other engagement features may from lower edges of the side panels 26, 126, 226 and back panels 22, 122, 222 of any of the other barriers in the present disclosure in any direction, quantity, or spacing, as appropriate for a given application.

Figure 9A:
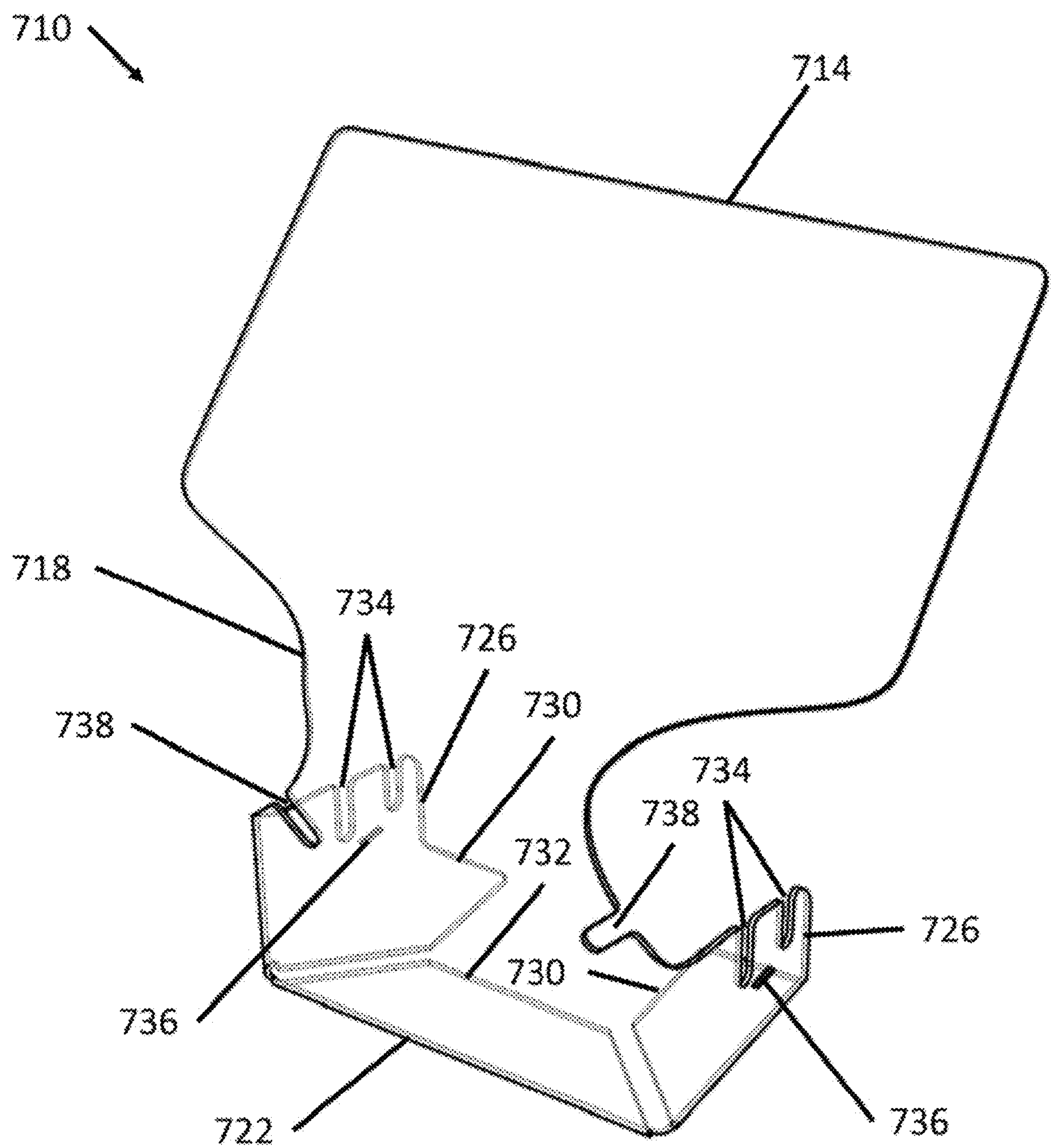
FIG. 9A is an oblique perspective view of a barrier according to an aspect of the disclosure.
Figure 9E:
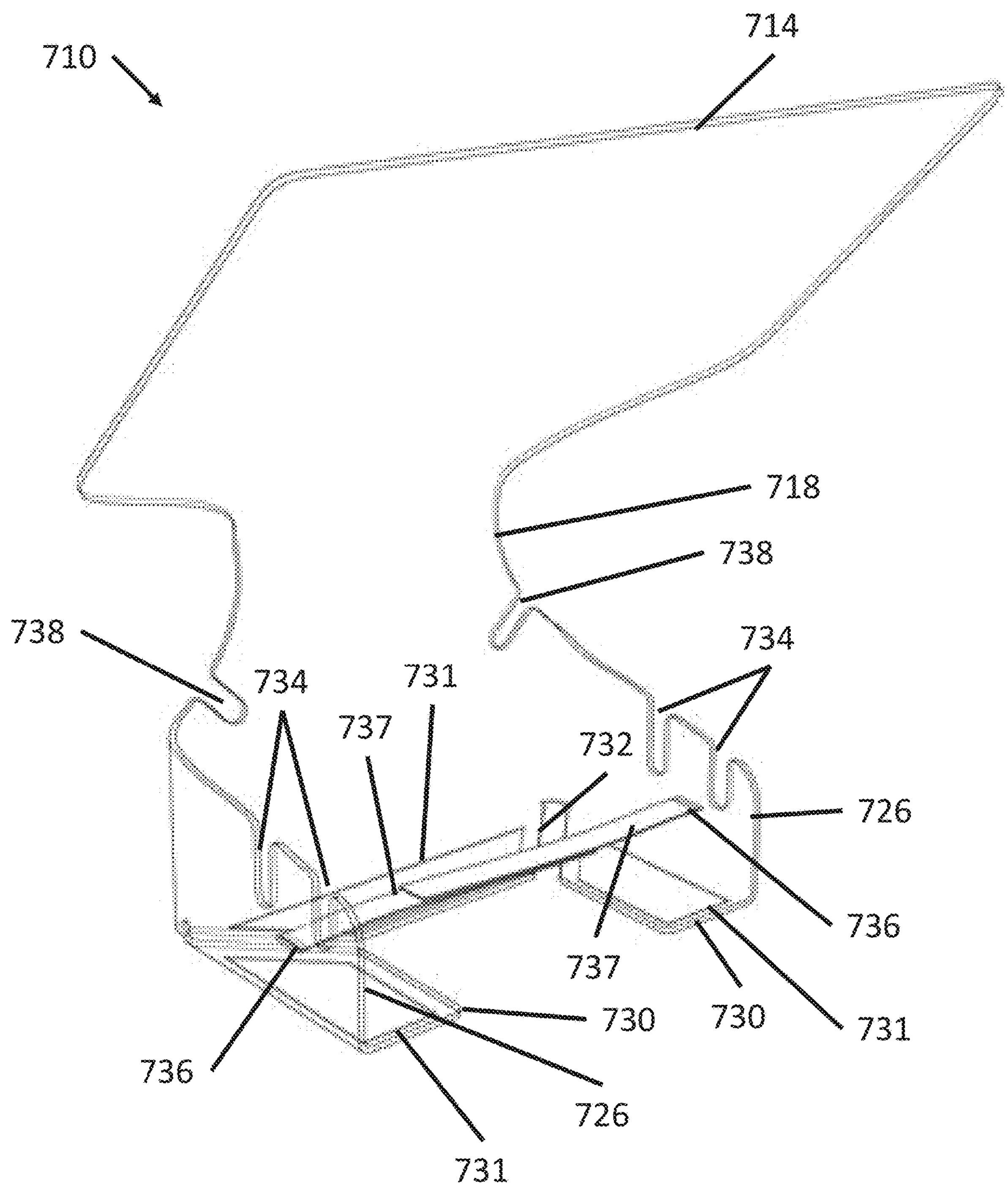
FIG. 9E is another oblique perspective view of the barrier of FIG. 9A with added attachments.
Figure 9F:
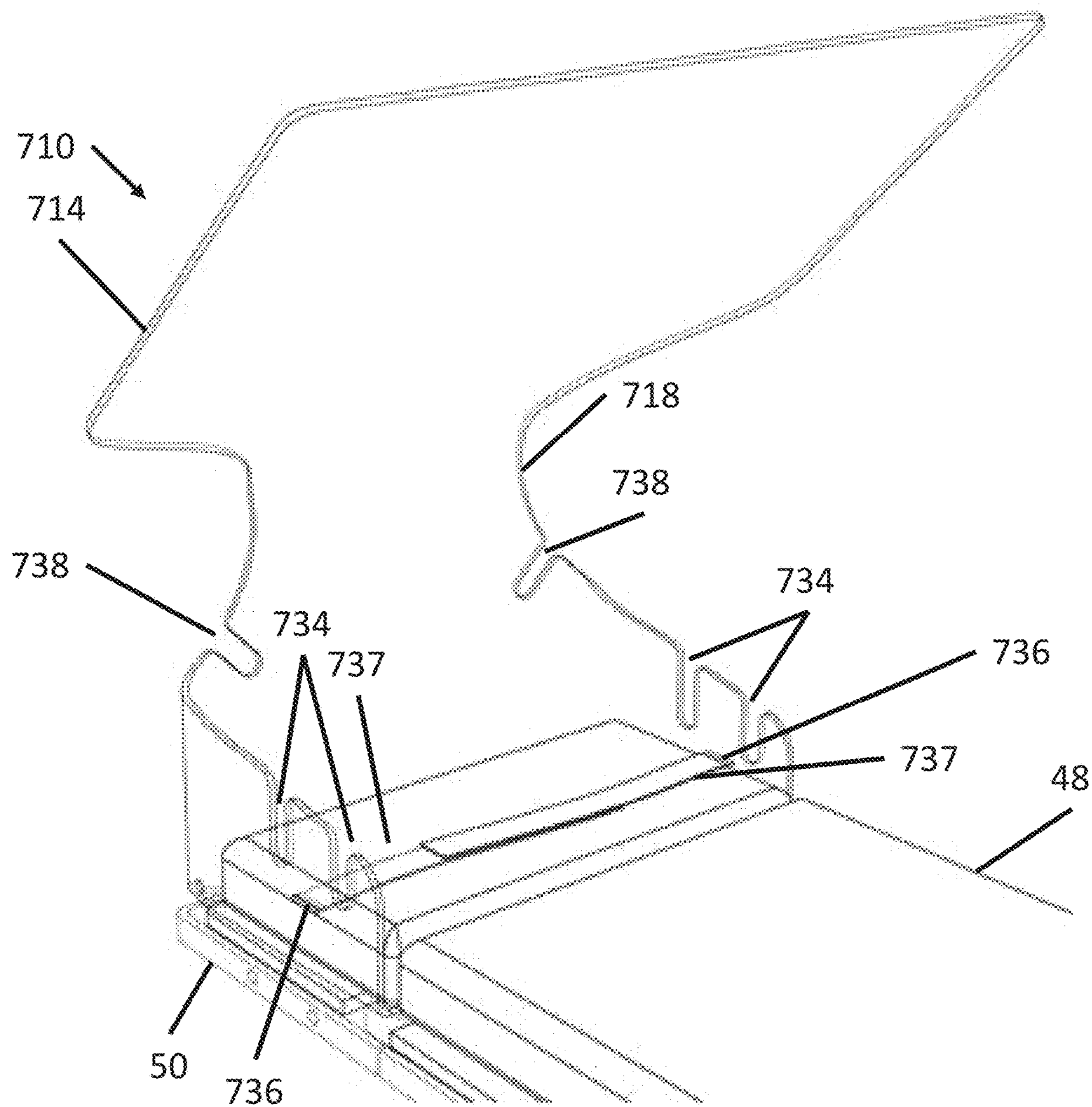
FIG. 9F illustrates the barrier of FIG. 9E retained to a mattress.
Figure 9G:
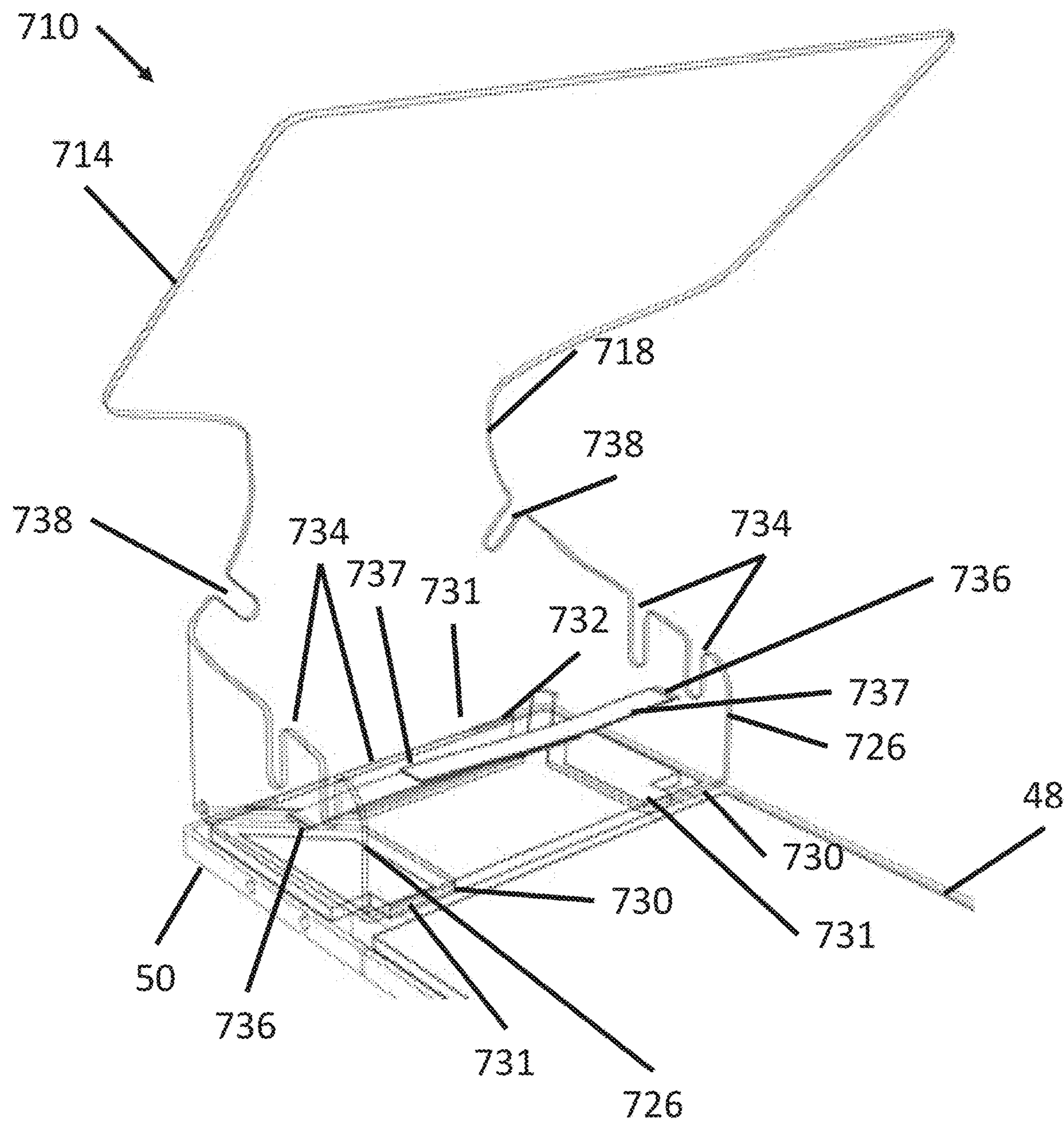
FIG. 9G illustrates the barrier of FIG. 9E retained to a bed frame.

FIGS. 9A-9H illustrate a barrier 710 according to yet another alternative arrangement. The barrier 710 includes a side flange 730 extending laterally inward at a 90° from a lower edge of each of the side panels 726 and a back flange 732 extending forward at a 90° from a lower edge of the back flange 722. Each of the side panels 726 further includes an aperture 736 through which a strap may be attached to the barrier 710. The flanges 730, 732 may slide under a mattress to be pinned to the bed frame by the weight of the mattress. The strap may be two opposed, mutually adhesible straps 737 (which may include, for example, microsuction tape, Velcro® or other hook and loop features) each secured in one of the apertures 736 as shown in FIG. 9E. The strap or straps may also extend over the mattress and under a pillow to cooperate with the flanges 730, 732 in holding the barrier 710 to the mattress as shown in FIG. 9F. In further examples, the strap is a disposable, adjustable strap, for example with Velcro or another adhesive enabling the adjustability, to wrap tightly around the mattress or headpiece. In alternative to or in combination with the foregoing, any or all of the panels 730, 732 may have adhesive patches 731 as shown in FIG. 9E. The adhesive patches 731 may be, for example, microsuction tape or mechanical adhesives such as Geckskin® on undersides of the flanges 730, 732 to adhere to the smooth surface of the bedframe as shown in FIG. 9G or on upper surfaces of the flanges to adhere to vinyl mattress covers.

Figure 9H:
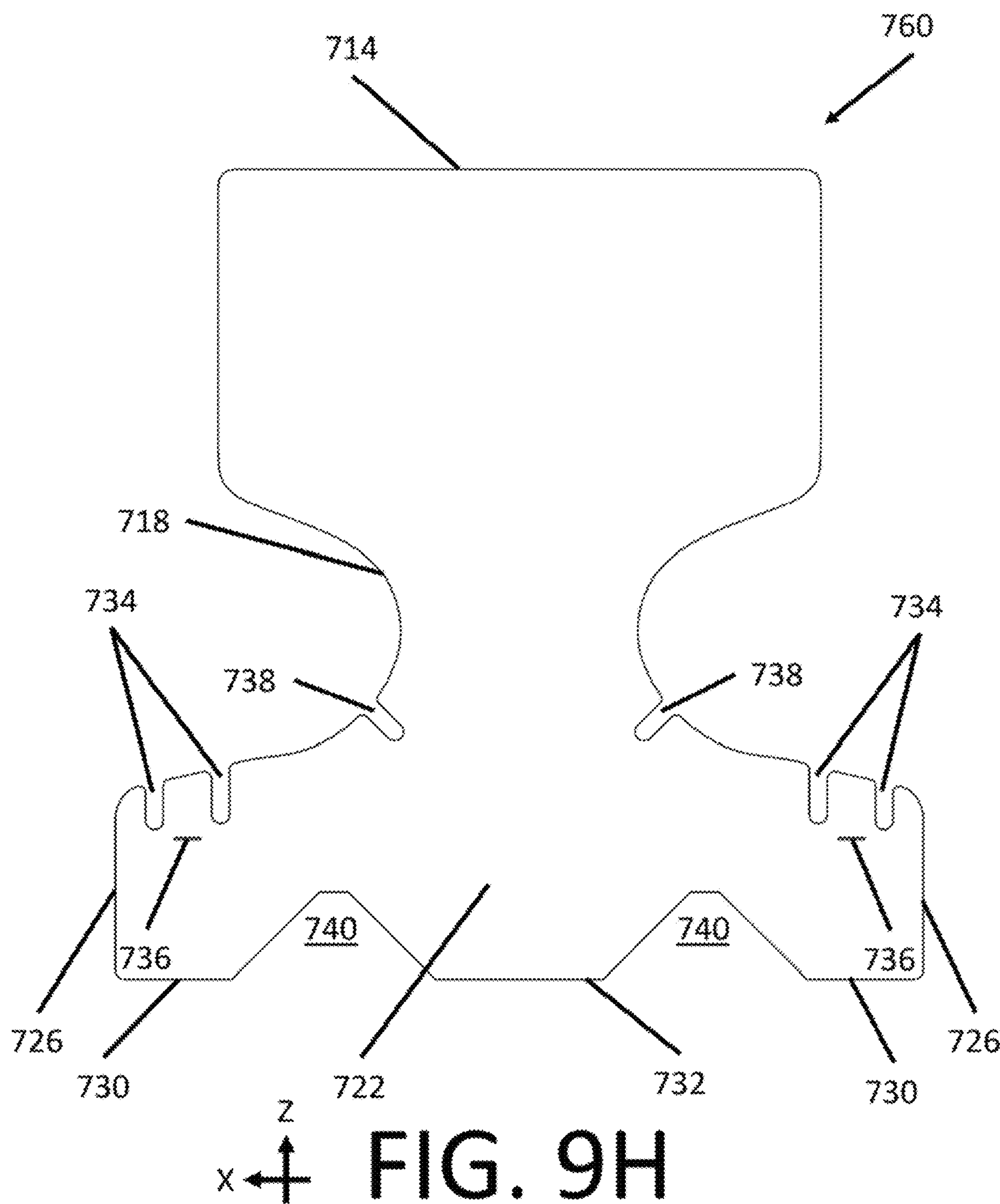
FIG. 9H is a plan view of a sheet as may be produced during an exemplary method of manufacturing the barrier of FIG. 9A.

FIG. 9H illustrates a shaped sheet 760 produced at a step of an exemplary method for manufacturing the barrier 710. The sheet 760 includes a pair of recesses 740 separating the back flange 732 from the side flanges 730. The process for manufacturing the barrier 710 includes bending the sheet 760 near the upper ends of the recesses 740 to put the flanges 730, 732 at final angles relative to their respective panels 722, 726. The adhesive patches 731 may be applied to the flanges 730, 732 before or after bending. Because the barrier 710 of FIGS. 9A-9F lacks mounting slots 30, mounting slots are not cut into the sheet 760 of FIG. 9H. Other than the foregoing differences, the process for manufacturing the barrier 710 of FIGS. 9A-9H is the same as the process for manufacturing the barrier 10 of FIG. 1A-1E.

Other elements of the barrier 710 of FIGS. 9A-9H correspond to the elements of the barrier 10 of FIGS. 1A-1F, and are therefore not enumerated or further detailed here. The flanges, apertures, and other features shown in FIG. 9A-9H or described with regard thereto may be implemented in any combination with any of the other barriers in the present disclosure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A barrier comprising:

two side panels extending on parallel planes and spaced laterally apart, each side panel including a back end, a front edge opposed to the back end, a bottom edge, and an engagement feature on the bottom edge of each side panel, an upper edge opposed to the bottom edge, and at least one slot extending downward from at least one of the upper edges;

a back panel connecting the side panels at the back ends; and a shield extending from an upper end of the back panel at an oblique angle in an upward and forward direction.

2. The barrier of claim 1, wherein the shield includes a neck that is laterally narrower than a distance between the two side panels and includes two opposed lateral sides and at least one slot extending into the neck from at least one of the two lateral sides.

3. The barrier of claim 1, wherein the shield includes a neck that is laterally narrower than a distance between the two side panels, the back panel is planar, and lateral sides of the neck are concave.

4. The barrier of claim 1, wherein the shield includes a shield panel that extends upwards from a neck adjoining the back panel and includes a lateral distance beyond a lateral distance of the side panels.

5. The barrier of claim 4, wherein a first wing and a second wing extend forward from each of two opposed lateral ends of the shield panel.

6. The barrier of claim 5, wherein the wings extend laterally outward and forward on oblique planes.

7. The barrier of claim 4, wherein the shield includes a curve such that the shield panel curves in the forward and upward direction with increasing distance from the back panel.

8. A method of manufacturing a barrier, the method comprising:

obtaining a planar sheet of transparent material, preparing a shape from the sheet, the shape including:

a lower base portion extending between two lower lateral edges, and a first tab and a second tab extending laterally from the two lower lateral edges of the lower base portion, each tab including a lower bottom edge including an engagement feature;

an upper portion extending between two upper lateral edges; and a neck joining the lower portion and the upper portion, the neck extending between two middle lateral edges, a distance between the middle lateral edges being less than a distance between the two lower lateral edges and a distance between the two upper lateral edges;

bending the tabs in a forward direction relative to a remainder of the lower portion; and bending at least one of at least a portion of the upper portion and at least a portion of the neck forward relative to the lower base portion.

9. The method of claim 8, wherein the upper portion includes lateral wing portions extending from each upper lateral edge inwardly towards a middle area of the upper portion, the method further comprising bending each lateral wing in the forward direction relative to a remainder of the upper portion.

10. The method of claim 8, wherein the step of bending at least one of at least the portion of the upper portion and at least the portion of the neck forward relative to the lower base portion includes introducing a curvature along a majority of the upper portion and along at least a portion of the neck.

11. The method of claim 8, wherein the step of bending at least one of at least the portion of the upper portion and at least the portion of the neck forward relative to the lower base portion includes introducing a bend on at least the portion of the upper portion or at least the portion of the neck, the remainder of the neck and upper portion on both the top and bottom of the bend are linear.

12. A method of intubating a patient, comprising:

observing the patient through a transparent barrier extending from a bed on which the patient lies and over the patient, the barrier including a lower base portion extending between two lower lateral edges, and a first tab and a second tab extending laterally from the two lower lateral edges of the lower base portion, each tab including a lower bottom edge including at least one slot extending upward from the lower bottom edge and an upper edge opposed to the bottom edge and at least one slot extending downward from at least one of the upper edges;

an upper portion extending between two upper lateral edges;

a neck joining the lower portion and the upper portion, the neck extending between two middle lateral edges, a distance between the middle lateral edges being less than a distance between the two lower lateral edges and a distance between the two upper lateral edges; and reaching around at least one of the middle lateral edges of the neck of the barrier to access the patient and/or manipulate a tube.

13. The method of claim 12, wherein at least one of the lateral middle edges includes at least one slot, the method further comprising the step of positioning the tube within the at least one slot.

14. A barrier comprising:

a lower base portion extending between two lower lateral edges, and a first tab and a second tab extending from the two lower lateral edges of the lower base portion, each tab including a lower bottom edge having an engagement feature;

an upper portion extending between two upper lateral edges; and a neck joining the lower portion and the upper portion, the neck extending between two middle lateral edges, a distance between the middle lateral edges being less than a distance between the two lower lateral edges and a distance between the two upper lateral edges.

15. The barrier of claim 14, wherein the engagement feature includes at least one slot extending upward from the lower bottom edge.

16. The barrier of claim 14, wherein at least a portion of each of the middle lateral edges is concave.

17. The barrier of claim 14, wherein each tab extends in a forward direction relative to a remainder of the lower base portion.

18. The barrier of claim 14, wherein at least one of at least a portion of the upper portion and at least a portion of the neck extend in a forward direction relative to the lower base portion.

19. The barrier of claim 14, wherein each tab includes an upper edge opposed to the lower edge of the respective tab, the upper edge of at least one tab includes at least one slot.

20. The barrier of claim 14, wherein the upper portion includes lateral wing portions extending from each upper lateral edge inwardly towards a middle area of the upper portion, each lateral wing portion extending in a forward direction relative to a remainder of the upper portion.

21. The barrier of claim 14, wherein a majority of the upper portion and at least a portion of the neck includes a curvature such that a top portion of the upper portion extends in a forward direction more than a bottom portion of the upper portion or the neck.

22. The barrier of claim 14, wherein at least a portion of the upper portion or at least a portion of the neck includes a bend, and a remainder of the neck and upper portion on both the top and bottom of the bend are linear.

* * * * *